(12) United States Patent
Levin et al.

(10) Patent No.: US 7,415,306 B2
(45) Date of Patent: Aug. 19, 2008

(54) TRANSDERMAL DELIVERY SYSTEM FOR ANTI-EMETIC MEDICATION

(75) Inventors: Galit Levin, Nordiya (IL); Dorit Daniel, Ra'anana (IL)

(73) Assignee: TransPharma Medical Ltd., Lod (IL)

( * ) Notice: Subject to any disclaimer, the term of this patent is extended or adjusted under 35 U.S.C. 154(b) by 134 days.

(21) Appl. No.: 11/116,065

(22) Filed: Apr. 27, 2005

(65) Prior Publication Data

US 2005/0260252 A1 Nov. 24, 2005

Related U.S. Application Data

(63) Continuation of application No. PCT/IL03/00902, filed on Oct. 30, 2003.

(30) Foreign Application Priority Data

Oct. 31, 2002 (IL) ........................... 152573

(51) Int. Cl.
*A61N 1/30* (2006.01)
(52) U.S. Cl. .................... 604/20; 604/21; 604/501
(58) Field of Classification Search .............. 604/21, 604/20, 501; 607/2, 3; 600/391, 372
See application file for complete search history.

(56) References Cited

U.S. PATENT DOCUMENTS

| 3,964,482 | A | 6/1976 | Gerstel et al. .............. 128/260 |
| 4,559,222 | A | 12/1985 | Enscore et al. ................ 424/28 |
| 4,668,232 | A | 5/1987 | Cordes et al. ................ 604/897 |
| 4,704,282 | A | 11/1987 | Campbell et al. ........... 424/449 |
| 4,867,982 | A | 9/1989 | Campbell et al. ........... 424/449 |
| 5,019,034 | A | 5/1991 | Weaver et al. ................ 604/20 |
| 5,152,997 | A | 10/1992 | Ebert et al. ................. 424/449 |
| 5,158,537 | A | 10/1992 | Haak et al. .................... 604/20 |
| 5,230,898 | A | 7/1993 | Hortsmann et al. ......... 424/449 |
| 5,320,597 | A | 6/1994 | Sage, Jr. et al. ............... 604/20 |
| 5,376,645 | A | 12/1994 | Stella et al. ................... 514/58 |
| 5,445,609 | A | 8/1995 | Lattin et al. ................... 604/20 |
| 5,460,820 | A | 10/1995 | Ebert et al. ................. 424/449 |

(Continued)

FOREIGN PATENT DOCUMENTS

WO WO 95/03764 2/1995

(Continued)

OTHER PUBLICATIONS

Yuri A. Chizmadzhev et al., "Electrical Properties of Skin at Moderate Voltages: Contribution of Appendageal Macropores", Biophysical Journal, vol. 74, pp. 843-856 (1998).

(Continued)

*Primary Examiner*—Sharon E. Kennedy
(74) *Attorney, Agent, or Firm*—Winston & Strawn LLP

(57) ABSTRACT

The present invention provides a transdermal delivery system for hydrophilic anti-emetic agents and methods of using thereof. The system includes an anti-emetic hydrophilic adhesive composition of a hydrophilic polymer and hydrophilic anti-emetic agent, a patch containing at least one hydrophilic layer of the composition, and an apparatus that generates hydrophilic micro-channels in skin of a subject using the patch or composition. The system preferably avoids the use of penetration enhancers and is particularly useful for transdermal delivery of hydrophilic anti-emetic agents.

33 Claims, 14 Drawing Sheets

U.S. PATENT DOCUMENTS

| | | | |
|---|---|---|---|
| 5,618,265 A | 4/1997 | Myers et al. | 604/20 |
| 5,622,944 A | 4/1997 | Hale et al. | 514/181 |
| 5,685,837 A | 11/1997 | Horstmann | 604/20 |
| 5,807,306 A | 9/1998 | Shapland et al. | 604/21 |
| 5,824,668 A | 10/1998 | Rubinfeld et al. | 514/170 |
| 5,840,327 A | 11/1998 | Gale et al. | 424/448 |
| 5,874,418 A | 2/1999 | Stella et al. | 514/58 |
| 5,885,211 A | 3/1999 | Eppstein et al. | 600/309 |
| 5,928,571 A | 7/1999 | Chan | 252/514 |
| 5,944,685 A | 8/1999 | Muroki | 604/20 |
| 5,983,130 A | 11/1999 | Phipps et al. | 604/20 |
| 5,983,135 A | 11/1999 | Avrahami | 604/20 |
| 5,989,586 A | 11/1999 | Hsu et al. | 424/449 |
| 5,993,435 A * | 11/1999 | Haak et al. | 604/501 |
| 6,004,578 A | 12/1999 | Lee et al. | 424/448 |
| 6,022,316 A | 2/2000 | Eppstein et al. | 600/309 |
| 6,046,177 A | 4/2000 | Stella et al. | 514/58 |
| 6,050,988 A | 4/2000 | Zuck | 604/890.1 |
| 6,083,196 A | 7/2000 | Trautman et al. | 604/46 |
| 6,132,760 A | 10/2000 | Hedenstrom et al. | 424/448 |
| 6,142,939 A | 11/2000 | Eppstein et al. | 600/309 |
| 6,148,232 A | 11/2000 | Avrahami | 604/20 |
| 6,169,920 B1 | 1/2001 | Haak et al. | 604/20 |
| 6,173,202 B1 | 1/2001 | Eppstein | 600/309 |
| 6,219,577 B1 | 4/2001 | Brown, III et al. | 604/20 |
| 6,317,629 B1 | 11/2001 | Haak et al. | 604/20 |
| 6,522,918 B1 | 2/2003 | Crisp et al. | 604/20 |
| 6,597,946 B2 | 7/2003 | Avrahami et al. | 604/20 |
| 6,611,706 B2 | 8/2003 | Avrahami et al. | 604/20 |
| 6,622,037 B2 | 9/2003 | Kasano | 604/20 |
| 6,662,044 B2 | 12/2003 | Crawford et al. | 604/20 |
| 2002/0010414 A1 | 1/2002 | Coston et al. | 604/20 |
| 2002/0038101 A1 | 3/2002 | Avrahami et al. | 604/20 |
| 2002/0058936 A1 | 5/2002 | Avrahami et al. | 604/20 |
| 2003/0139731 A1 | 7/2003 | Marchitto et al. | 604/890.1 |
| 2003/0204163 A1 | 10/2003 | Marchitto et al. | 604/65 |
| 2004/0059282 A1 | 3/2004 | Flock et al. | 604/20 |

FOREIGN PATENT DOCUMENTS

| | | |
|---|---|---|
| WO | WO 96/16659 | 6/1996 |
| WO | WO 97/07734 | 3/1997 |
| WO | WO 97/24148 | 7/1997 |
| WO | WO 98/37871 | 9/1998 |
| WO | WO 98/53815 | 12/1998 |
| WO | WO 00/47208 | 8/2000 |
| WO | WO 00/76522 A1 | 12/2000 |
| WO | WO 01/85234 A2 | 11/2001 |
| WO | WO 02/17927 A1 | 3/2002 |
| WO | WO 02/085451 A2 | 10/2002 |
| WO | WO 02/092163 A2 | 11/2002 |

OTHER PUBLICATIONS

US 6,214,374, 04/2001, Schmirler et al. (withdrawn)

\* cited by examiner

TRANSDERMAL DELIVERY SYSTEM FOR ANTI-EMETIC MEDICATION

CROSS-REFERENCE TO RELATED APPLICATION

This application is a continuation of International application PCT/IL2003/000902 filed Oct. 30, 2003, the entire content of which is expressly incorporated herein by reference thereto.

FIELD OF THE INVENTION

The present invention relates generally to the field of drug formulations for use in conjunction with a transdermal delivery apparatus and relates specifically to a drug-containing matrix that is useful as a component in a transdermal delivery system for effective sustained action of anti-emetic medications, in conjunction with an apparatus that operates by forming micro-channels in the skin.

BACKGROUND OF THE INVENTION

Drug delivery across the skin of a patient obviates a variety of problems associated with oral administration of the drug, for example, nausea or vomiting, drug inactivation by gastrointestinal enzymes, and fluctuations in blood concentrations of the drug resulting from fluctuations in absorption from the gastrointestinal tract, and from hepatic first pass inactivation. Drug delivery across the skin of a patient also avoids the inconvenience associated with drug injection.

Transdermal drug delivery has been tackled using one of the two complementary approaches known in the art. One approach utilizes a method of puncturing the skin or otherwise disrupting the impermeable layers of the skin to facilitate the entry of drugs into the systemic circulation, and the other approach provides formulations of drugs that may be applied to the skin in the form of patches, films or matrices of varying compositions.

Transdermal Delivery Apparatus

Electrotransport or iontophoretic drug delivery devices have been disclosed as being useful for the delivery of many types of drugs for which it is anticipated that transdermal delivery would be advantageous. U.S. Pat. Nos. 6,169,920 and 6,317,629 to Alza for example disclose iontophoretic drug delivery apparatus, and U.S. Pat. No. 5,983,130 to Alza discloses an electrotransport agent delivery method and apparatus suitable for ionizable drugs.

Electroporation is also well known in the art as a method to increase pore size by application of an electric field. Electroporation is disclosed as a means for transiently decreasing the electrical resistance of the stratum corneum and increasing the transdermal flux of small molecules by applying an electric field to increase the size of existing pores (Chizmadzhev et al., Biophysics Journal, 1998,74 (2), 843-856).

U.S. Pat. No. 5,019,034 to Weaver et al. describes apparatus for applying high voltage, short duration electrical pulses on the skin to produce electroporation.

WO 97/07734 to Eppstein et al. discloses thermal ablation of the stratum corneum using an electrically resistive element in contact with the stratum corneum, such that a high current through the element causes a general heating of tissue in its vicinity, most particularly the stratum corneum, that is the 10-50 micron thick outermost layer of the skin.

U.S. Pat. Nos. 5,885,211, 6,022,316, 6,142,939 and 6,173,202 to Eppstein et al., which are incorporated herein by reference, describe methods for forming micro-pores in the stratum corneum by heating tissue-bound water above the vapor point with a heat-conducting element, so as to enhance transdermal transport of an analyte or active substance. Further enhancement techniques include the use of sonic energy, pressure, and chemical enhancers.

U.S. Pat. No. 3,964,482 to Gerstel, U.S. Pat. No. 6,050,988 to Zuck, and U.S. Pat. No. 6,083,196 to Trautman et al. describe other apparatus and methods for facilitating transdermal movement of a substance.

U.S. Pat. No. 6,148,232 to Avrahami, which is incorporated herein in its entirety by reference, describes a device for ablating the stratum corneum of a subject. The device includes a plurality of electrodes, which are applied at respective points on skin of a subject. A power source applies electrical energy between two or more of the electrodes to cause ablation of distinct regions of the stratum corneum (SC), primarily beneath the respective electrodes. Various techniques for limiting ablation to the stratum corneum are described, including spacing of the electrodes and monitoring the electrical resistance of skin between adjacent electrodes. The device disclosed in U.S. Pat. No. 6,148,232 and continuations thereto (U.S. Pat. Nos. 5,983,135; 6,579,946; and 6,611,706, and International Patent Applications Nos. WO 01/85234, WO 02/085451 and WO 02/092163 are referred hereinafter in the specification by the name ViaDerm.

Transdermal Patches

There are two prevalent types of transdermal patch designs, namely the reservoir type where the drug is contained within a reservoir having a basal surface that is permeable to the drug, and a matrix type, where the drug is dispersed in a polymer layer affixed to the skin. Both types of designs also typically include a backing layer and an inner release liner layer that is removed prior to use.

Patches usually comprise penetration enhancers and adhesive layers, which known to cause irritation or edema. In addition, patches are known to produce non-uniform rates of drug release between different patients and different skin types.

U.S. Pat. No. 4,668,232 describes a matrix for a transdermal patch, which comprises a reservoir layer comprising a water-swellable polymeric matrix composed of an adhesive material, and a drug that is partially or wholly soluble in the adhesive material. The inclusion of the water-swellable polymer is alleged to increase the release rate of the drug from the matrix.

U.S. Pat. No. 5,230,898 describes a transdermal patch comprising a matrix composed of a water-insoluble material that contains islands of solid particles of a drug in a water-soluble/swellable polymer and an underlayer that controls the amount of water vapor passing from the skin to the matrix. The matrix is said to be activated by water vapor from the skin.

U.S. Pat. No. 4,559,222 describes a transdermal matrix-type patch in which the matrix is composed of a mixture of mineral oil, polyisobutylene (an adhesive), and colloidal silicon dioxide. The addition of the silicon dioxide allegedly affects the flow characteristics of the mineral oil-polyisobutylene mix.

Compositions or devices in the form of specific types of patches adapted for the transdermal delivery of anti-emetics include: U.S. Pat. No. 5,989,586 that discloses a transdermal patch comprising two-phase drug-containing matrix for sustained release of the drug; WO 00/47208 that discloses a transdermal composition comprising a matrix containing an alcohol, a penetration enhancer, water, and an anti-vomiting agent selected from tropisetron, ondansetron and granisetron; and WO 98/53815 that discloses a transdermal delivery device for the delivery of tropisetron or granisetron comprising an adhesive layer comprising specific alkylacrylates and hydrophilic monomers.

There remains an unmet medical need to overcome skin trauma, pain and uncontrollable delivery rate encountered with patches known in the art, and to provide a transdermal delivery system for hydrophilic drugs, which enables increased drug efficacy and sustained activity.

SUMMARY OF THE INVENTION

The present invention relates to an effective system and methods for transdermal delivery of an active anti-emetic agent. The present invention further relates to apparatus and methods for ablating the skin and transdermally delivering an active anti-emetic agent to the pretreated skin.

In particular, the present invention relates to apparatus and methods for transdermally delivering an active anti-emetic agent using a suitable medical patch. More particularly, the present invention relates to apparatus and methods for ablating the skin and transdermally delivering an active anti-emetic agent using a hydrophilic medical skin patch.

The compositions and the methods of the present invention are suitable for use with many of the patches known in the art, though application of the drug with the system of the present invention has proven particularly effective and has yielded unexpectedly advantageous clinical results.

It is now disclosed for the first time that use of a hydrophilic patch comprising a hydrophilic anti-emetic drug, placed on an area of the skin pretreated by an apparatus that generates micro-channels provides unexpectedly long lasting therapeutically effective serum levels of the drug accompanied with negligible irritation. This system has further yielded unexpectedly low patient-to-patient variation. Thus, the system and methods of the present invention provide for the first time a reliable transdermal delivery of hydrophilic anti-emetic drugs with reproducible controlled or sustained drug action.

The principles of the invention are exemplified herein below using a hydrophilic derivative of granisetron. It is explicitly intended that the compositions and methods comprising the system of the invention are applicable to a wide variety of hydrophilic anti-emetic agents.

According to one aspect, the present invention provides a system for transdermal delivery of a hydrophilic anti-emetic agent comprising an apparatus for facilitating transdermal delivery of a hydrophilic anti-emetic agent through skin of a subject, said apparatus capable of generating at least one micro-channel in an area on the skin of the subject; and a patch comprising at least one hydrophilic layer comprising a therapeutically effective amount of the hydrophilic anti-emetic agent in a pharmaceutical composition.

According to certain preferred embodiments, the present invention incorporates the techniques for creating micro-channels by inducing ablation of the stratum corneum, using radio frequency (RF) energy, including the apparatus referred to as ViaDerm or MicroDerm, disclosed in one or more of the following: U.S. Pat. No. 6,148,232 to Avrahami; U.S. Pat. No. 5,983,135 to Avrahami; WO 01/85234; U.S. Pat. No. 6,597, 946; U.S. Pat. No. 6,611,706; WO 02/085451; and WO 02/092163, the content of which is incorporated herein in their entirety. It is however emphasized that although some preferred embodiments of the present invention relate to transdermal delivery obtained by ablating the skin by the aforementioned apparatus, substantially any method known in the art for generating channels in the skin of a subject may be used.

In one embodiment of the invention, the system comprises an apparatus for facilitating transdermal delivery of a drug through the skin of a subject using Radio Frequency (RF) energy, said apparatus comprising:
 a. an electrode cartridge, optionally removable, comprising at least one electrode; and
 b. a main unit comprising a control unit which is adapted to apply electrical energy to the electrode when the electrode is in vicinity of the skin, typically generating current flow or one or more sparks, enabling ablation of stratum corneum in an area beneath the electrode, thereby generating at least one micro-channel.

In another embodiment, the control unit of the apparatus comprises circuitry to control the magnitude, frequency, and/or duration of the electrical energy delivered to an electrode, so as to control the current flow or spark generation, and thus the width, depth and shape of the formed micro-channel. Preferably, the electrical energy is at radio frequency.

In a currently preferred embodiment, the electrode cartridge of the apparatus comprises a plurality of electrodes enabling to generate a plurality of micro-channels, wherein the micro-channels are of uniform shape and dimensions.

The term "micro-channel" as used in the context of the present patent application refers to a pathway, generally extending from the surface of the skin through all or significant part of the stratum corneum, through which molecules can diffuse.

According to the invention, the transdermal delivery system comprises a patch comprising a hydrophilic anti-emetic agent wherein said patch is placed over the treated region in which the micro-channels were generated. The patch may further comprise at least one layer selected from a backing layer, an adhesive, and a release liner. The patch may further be of any suitable geometry provided that it is adapted for stable, and optionally microbiologically controlled, aseptic or sterile, storage of the drug species prior to its use.

In a further embodiment, the anti-emetic agent is selected from the group of dopamine antagonists, acetylcholine receptor antagonists, 5-hydroxytryptamine receptor antagonists, and pharmaceutically acceptable salts, and hydrates thereof.

In another embodiment, the anti-emetic agent is 5-hydroxytryptamine receptor antagonist selected from the group consisting of hydrophilic derivatives of granisetron, ondansetron, dolasetron, lerisetron, tropisetron, itasetron and ramosetron. In a currently preferred embodiment, the anti-emetic agent is granisetron hydrochloride.

In a preferred embodiment, the hydrophilic layer of the patch comprises at least one hydrophilic polymer. The polymer is capable of adsorbing a solution of the anti-emetic agent. In another embodiment, the hydrophilic polymer is selected from the group consisting of cellulose, hydroxy cellulose, carboxymethyl cellulose, hydroxyethyl cellulose, hydroxypropyl cellulose, hydroxypropylmethyl cellulose, polysaccharides, chitin, chitosan, diacylated chitin, gum acacia, agarose, carrageenan, gelatin, gum tragacanth, alginate, karaya gum, veegum, pectin, hyaluronic acid, pluronic acid, maltodextrin, polyvinylpyrrolidone, polyglycolic acid, polyoxyethylene, polyoxypropylene, colloidal silicon dioxide, polyvinyl alcohol, polyacrylamide, polyacrylic acid, polyacrylates, methacrylate polymers, fumed silica, and a like. The pharmaceutical composition may further comprise at least one component selected from a plasticizer, a cross-linker, a buffering agent, a stabilizer, and an anti-oxidant. The pharmaceutical composition according to certain embodiments may advantageously be devoid of penetration enhancers.

In another aspect, the present invention provides an anti-emetic hydrophilic adhesive composition comprising a hydrophilic polymer and a hydrophilic anti-emetic agent, devoid of penetration enhancers. The hydrophilic polymer according to the invention may be selected from the group consisting of cellulose, hydroxy cellulose, carboxymethyl cellulose, hydroxyethyl cellulose, hydroxypropyl cellulose, hydroxypropylmethyl cellulose, polysaccharides, chitin, chitosan, diacylated chitin, gum acacia, agarose, carrageenan, gelatin, gum tragacanth, alginate, karaya gum, veegum, pectin, hyaluronic acid, pluronic acid, maltodextrin, polyvinylpyrrolidone, polyglycolic acid, polyoxyethylene, polyoxypropylene, colloidal silicon dioxide, polyvinyl alcohol, polyacrylamide, polyacrylic acid, polyacrylates, methacrylate polymers, fumed silica, and any adhesive polymer known in the art.

In another embodiment, the anti-emetic hydrophilic adhesive composition comprises an anti-emetic agent selected from the group of dopamine antagonists, acetylcholine receptor antagonists, 5-hydroxytryptamine receptor antagonists, and pharmaceutically acceptable salts, and hydrates thereof.

In another embodiment, the anti-emetic agent in the adhesive composition is 5-hydroxytryptamine receptor antagonist selected from the group consisting of hydrophilic derivatives of granisetron, ondansetron, dolasetron, lerisetron, tropisetron, itasetron and ramosetron. In a currently preferred embodiment, the anti-emetic agent is granisetron hydrochloride.

The adhesive composition may further comprise at least one component selected from a plasticizer, a cross-linker, a buffering agent, a stabilizer, and an anti-oxidant.

In another embodiment, the present invention provides a patch comprising at least one hydrophilic layer comprising a hydrophilic anti-emetic agent and a hydrophilic polymer, devoid of penetration enhancers. In a currently preferred embodiment, the hydrophilic polymer is selected from polyethylene oxide, polyvinylpyrrolidone, and hydroxypropylmethyl cellulose. The patch may further comprise at least one layer selected from a backing layer, an adhesive layer that enables the patch to be affixed to the skin, and a release liner.

The simplicity of the essential ingredients of the patch stems from the fact that the patch is specifically designed for use in conjunction with the apparatus for generating micro-channels in the skin of the subject.

According to additional aspect, the present invention provides a method of transdermal administration of a hydrophilic anti-emetic agent using a patch according to embodiments of the present invention. In one embodiment the method comprises: generating at least one micro-channel in an area of the skin of a subject, and affixing a patch to the area of skin in which the micro-channels are present, the patch comprising at least one hydrophilic layer comprising a therapeutically effective amount of an anti-emetic agent. The method of the invention achieves serum concentration of at least 1 ng/ml of the anti-emetic agent. Preferably, the serum concentration of at least 1 ng/ml of the anti-emetic agent is maintained over a period of at least 24 hours, and more preferably for a period of at least 48 hours.

In currently preferred embodiment of the present invention, the hydrophilic anti-emetic agent is selected from the group consisting of dopamine antagonists, including but not limited to, metoclopramide hydrophilic derivatives such as metoclopramide dihydrochloride monohydrate and metoclopramide monohydrochloride monohydrate; acetylcholine receptor antagonists including, without limitation, scopolamine hydrophilic derivatives such as scopolamine hydrochloride, scopolamine methyl nitrate; hydrophilic derivatives of 5-hydroxytryptamine (5HT3) receptor antagonists including, but not limited to, granisetron hydrochloride, ondansetron hydrochloride dihydrate, dolasetron hydrophilic derivatives, lerisetron hydrophilic derivatives, tropisetron monohydrochloride, itasetron hydrochloride, ramosetron hydrochloride. The invention includes all pharmaceutically acceptable salts, and hydrates of these agents.

A currently more preferred embodiment exemplified herein below is a hydrophilic derivative of granisetron.

The present invention will be more fully understood from the following detailed description of the preferred embodiments thereof.

DETAILED DESCRIPTION OF THE INVENTION

Figure 1:
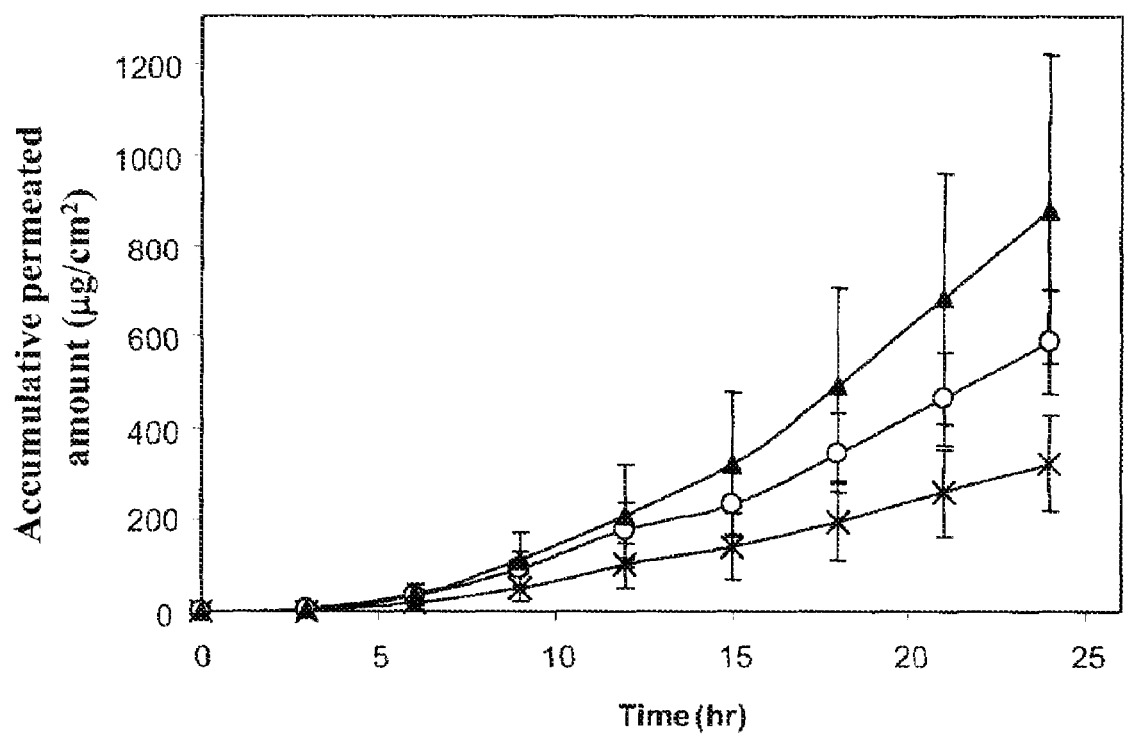
FIG. 1 shows permeation of granisetron, applied by means of a solution or commercially available hydrogels, through porcine ear skin after generation of micro-channels. Solution 5% (▲); NUGEL™ (x); VIGILON™ (○).

The present invention provides formulations, methods and pharmaceutical technologies for delivering anti-emetic agents through treated skin in which hydrophilic micro-channels have been generated.

Previously known transdermal patches are designed to deliver drug molecules through the stratum corneum (SC). As such they have several characteristics:

a. The delivery of the molecules occurs through all the area under the patch.

b. The interface between the patch and the skin tends to be hydrophobic. This facilitates movement of drug molecules from one hydrophobic matrix (patch) to the other (SC).

c. The patches usually contain enhancers. The purpose of these molecules is to change and disrupt the structure of the SC, thus elevating the solubility of the drug molecules in the SC. Enhancers are also responsible for undesired side-effects like erythema, edema or pruritis.

Micro-channels are aqueous passages through the SC into the epidermis, thus drug molecules do not need to pass through the hydrophobic SC in order to get into viable tissues. This has several implications:

1. The transdermal delivery of very hydrophilic molecules is feasible.
2. The delivery of the molecules occurs mainly through the micro-channels, which occupy less than 1% of the treated skin area.
3. The drug molecules need to diffuse into a hydrophilic medium, therefore hydrophilic matrices are more suitable.
4. There is no need to include penetration enhancers in the formulations, thus improving skin safety.
5. The delivery from aqueous solutions is very efficient.

Based on these considerations, the system of the present invention is highly suitable for delivery of various anti-emetic agents through the new skin environment, which is created by the ablation of the stratum corneum using RF energy. Accordingly, a variety of formulations may provide efficient delivery of a variety of anti-emetic agents, particularly and advantageously of hydrophilic formulations, without being penetration-limited by the resistance of the lipophilic outmost layer of the skin. As a consequence, the system of the present invention does not require the use of permeation enhancers for transdermal drug delivery and is therefore not susceptible to the problems attendant therewith, particularly irritation. Irritation occurs as the skin reacts to topically applied substances, particularly those maintained under occlusion, by blistering or reddening accompanied by unpleasant burning, itching, and stinging sensations. It is desirable to avoid or to keep the number of possibly irritating substances in a transdermal delivery system to a minimum.

The term "micro-channel" as used in the context of the present specification and claims refers to a pathway generally extending from the surface of the skin through all or a significant part of the stratum corneum, through which molecules can diffuse. Although some preferred embodiments of the present invention are described with respect to ablating the stratum corneum by electric current or spark generation using RF energy, substantially any method known in the art for generating channels in the skin of a subject may be used (see e.g. U.S. Pat. Nos. 5,885,211; 6,022,316; 6,142,939; 6,173,202; 6,148,232; and WO 02/085451 and WO 02/092163). The term "micro-pore" is used interchangeably herein.

Suitable anti-emetic agents for use in conjunction with the principles of the invention are hydrophilic anti-emetic agents, pharmaceutically acceptable salts, hydrates, and hydrophilic derivatives thereof. The anti-emetic agents include, but not limited to, dopamine antagonists, including metoclopramide hydrophilic derivatives such as metoclopramide dihydrochloride monohydrate and metoclopramide monohydrochloride monohydrate; acetylcholine receptor antagonists, including without limitation scopolamine hydrophilic derivatives such as scopolamine hydrochloride, scopolamine methyl nitrate; hydrophilic derivatives of 5-hydroxytryptamine (5HT3) receptor antagonists including, but not limited to, granisetron hydrochloride, ondansetron hydrochloride dihydrate, tropisetron monohydrochloride, itasetron hydrochloride, ramosetron hydrochloride, lerisetron hydrophilic derivatives, dolasetron hydrophilic derivatives.

As used herein, "a pharmaceutically acceptable salt" refers to a derivative of the disclosed agents wherein the parent agent is modified by making acid or base salts of the agent. For example, acid salts are prepared from the free base (typically wherein the neutral form of the drug has a neutral —NH$_2$ group) using conventional means known in the art, involving reaction with a suitable acid. Suitable acids for preparing acid salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. Conversely, preparation of basic salts of acid moieties which may be present on a drug are prepared using a pharmaceutically acceptable base such as sodium hydroxide, potassium hydroxide, ammonium hydroxide, calcium hydroxide, trimethylamine, or the like.

Additionally, the present invention encompasses esters and amides of the anti-emetic agents so long as the ester and amide derivatives retain an anti-emetic activity. Preparation of esters involves functionalization of hydroxyl and/or carboxyl groups, which may be present within the molecular structure of the agent. The esters are typically acyl-substituted derivatives of free alcohol groups, i.e., moieties that are derived from carboxylic acids of the formula RCOOH where R is alkyl, and preferably is lower alkyl. Esters can be reconverted to the free acids, if desired, by using conventional hydrogenolysis or hydrolysis procedures. Preparation of amides can be carried out in an analogous manner.

Other hydrophilic derivatives and analogs of the active agents may be prepared using standard techniques known to those skilled in the art of synthetic organic chemistry, or may be deduced by reference to the pertinent literature. In addition, chiral active agents may be in isomerically pure form, or they may be administered as a racemic mixture of isomers.

One currently preferred embodiment exemplified herein below is a hydrophilic derivative of granisetron, more preferably granisetron hydrochloride (HCl).

In a preferred embodiment of the present invention, the anti-emetic drug composition can comprise more than one anti-emetic pharmaceutical agent. It is known in the art that a combination of 5HT3 receptor antagonists with neurokinin I (NKI) receptor antagonists or with corticosteroids may be advantageous. Corticosteroids are hydrophobic, and therefore to be useful in the composition and methods of the invention the corticosteroids may be formulated as inclusion complexes in cyclodextrins or otherwise converted to a hydrophilic form. Alternatively, steroids may be administered in parallel rather than as part of a singly pharmaceutical composition.

As used herein, "pharmaceutical composition" or "medication" or "drug" used herein interchangeably, refer to a pharmaceutical composition comprising a therapeutically effective amount of an anti-emetic agent of the invention.

The pharmaceutical composition for use according to principle of the invention can be optimized to take into consideration issues like stability or adhesive properties. In this specification the term "stable" refers to a composition that is robust enough to retain at least 80% of the active ingredient in its original chemical form for a period of over 12 months at ambient temperatures.

To achieve stability, the pharmaceutical composition may include one or more enzyme inhibitors effective to inhibit drug-degrading enzymes, which may be released after the generation of the micro-channels. Such enzyme inhibiting compounds may be determined by those skilled in the art by reference to the pertinent literature and/or using routine experimental methods.

Matrices and Patches Suitable for Delivery of Hydrophilic Anti-Emetic Drugs

The system of the present invention includes a skin or pharmaceutical patch. Preferably, the patch is placed over the new skin environment. The term "new skin environment" as used herein, denotes a skin region created by the ablation of the stratum corneum and formation of at least one micro-channel, using the system of the present invention.

Thus, several general embodiments are covered by the invention, including embodiments in which the patch comprises a self-adhesive drug-containing layer, and in which the patch comprises an inert (not containing a drug) self-adhesive layer, and a non-adhesive layer that contains the anti-emetic medication that is attached to the inert adhesive layer.

The patch of the present invention may comprise any suitable arrangement and geometry. The patch according to the present invention should maintain the pharmaceutical composition under stable, optionally microbiologically controlled, aseptic or sterile conditions.

Advantageously, the hydrophilic character of the patch enables improved delivery of the anti-emetic medication in the absence of permeation enhancers.

The patch according to the present invention comprises a hydrophilic layer comprising a hydrophilic polymer and a hydrophilic anti-emetic agent in a pharmaceutically active composition.

Thus, in a preferred embodiment of the present invention, the anti-emetic pharmaceutically active composition contains at least one hydrophilic polymer capable of adsorbing a solution of at least one anti-emetic agent and consequently forming a three-dimensional (3-D) solid matrix, comprising the pharmaceutically active agents.

In a most preferred embodiment, hydrogel is used as the matrix that holds the drug. The term "hydrogel" refers to a 3-D, hydrophilic, network, which has cross-linked structures and is capable of imbibing large amounts of water or any biological fluid. As a result of absorbing a large amount of fluid the 3-D network swells to form a substantially water-insoluble hydrogel. Most preferably, the hydrogel of the present invention is a polyethylene oxide based gel (as exemplified herein below by. VIGILON™, The Medical Supply Company Inc., NY, USA) or polyvinylpyrrolidone (as exemplified herein below by NUGEL™, Johnson & Johnson, USA).

Other hydrophilic polymers that may be used in accordance with the present invention may be selected from biopolymers and hydrophilic synthetic polymers including, but not limited to, cellulose, carboxymethyl cellulose, hydroxyethyl cellulose, hydroxypropyl cellulose, hydroxypropylmethyl cellulose, polysaccharides, chitin, chitosan, gum acacia, agarose, carrageenan, gelatin, gum tragacanth, alginate, karaya gum, veegum, pectin, hyaluronic acid, pluronic acid, maltodextrin, polyvinylpyrrolidone, polyglycolic acid, polyoxyethylene, polyoxypropylene, colloidal silicon dioxide, polyvinyl alcohol, polyacrylamide, polyacrylic acid (or its salts), polyacrylates, fumed silica and the like. It should be appreciated that the hydrophilic layer according to the present invention comprises at least one hydrophilic polymer. Hence mixture or chemical conjugates of different hydrophilic polymers to form the hydrophilic layer are encompassed in the present invention.

The pharmaceutical composition, incorporated within the hydrophilic layer, may not be self-adherent and hence the patch may further comprise an adhesive. Adhesives that can be used in accordance with the present invention include methacrylate polymers, polyacrylates, carbopol, hydroxy celluloses and polysaccharides such as hydroxypropyl cellulose, hydroxyethyl cellulose, hydroxypropylmethyl cellulose, pectin, calcium pectinate, alginic acid, calcium alginate, cellulose acetate phthalate, guar gum, gum tragacanth, gum acacia, other vegetable gums, diacylated chitin, and any other adhesive polymer known in the art. The preferred adhesives are acrylic acid polymers and polymetacrylates. Most preferred adhesives are selected from the group of polymers based on 2-dimethyl aminoethyl methacrylate, methyl methacrylate and n-butyl methacrylate.

Other hydrogel compositions that may be used according to the invention are known in the art (see International Patent Application WO 00/196422, which discloses high water content hydrogel compositions and processes of making them using photopolymerization). The degree of polymerization and/or cross-linking of a hydrophilic polymer according to the invention may be varied according to the desired skin adhesion properties of the pharmaceutically active compositions and/or the patch (see International Patent Application WO 00/45864 and U.S. Pat. No. 5,665,477. U.S. Pat. No. 5,665,477 discloses a biocompatible hydrogel adhesive, which is prepared by polymerizing a composition comprising acrylic acid monomer and an alcohol amine. The resultant hydrogel adheres to both wet and dry tissues). Cross-linking of a hydrophilic polymer is well known in the art. Alternatively, the polymeric materials according to the invention do not need to be cross-linked.

The amount of an anti-emetic agent in the pharmaceutical composition necessary to provide the desired amounts and concentrations in the serum can be determined by known methods. Thus, the concentration and the quantity of the pharmaceutically active agent per solution, per matrix and per patch can be varied independently in order to achieve a desired effect.

The pharmaceutically active composition, incorporated into hydrophilic polymer, preferably hydrophilic cross-linked polymers, may be further incorporated into medical patches. The pharmaceutical composition may additionally comprise preservatives, plasticizers, anti-oxidants, buffering agents, and other additives as are well known in the art.

Optionally, the medical patch further comprises at least one of the following layers: a backing layer, an adhesive, and a release liner. The drug-containing layer may be disposed between the backing layer and the liner layer.

The term "backing layer" refers to any protective layer not permeable to the drug that is provided to physically seal and hence protect the patch, specifically, the drug containing layer. The backing layer may be made of a polyester, polyethylene or polypropylene. Application of a patch to the new skin environment is accomplished after at least partial removal of a release liner, before use. This exposes the drug-containing layer, which may itself have adhesive properties, or may further comprise an adhesive layer attached to the drug-containing layer. Proper adherence to usage instructions generally ensures avoidance of infections.

The plasticizers, which may be contained in the patch of the present invention, include, but are not limited to, triethyl citrate, dibutylphthalate, diethylphthalate, acetyltriethyl citrate, tributyl citrate, dibutyl sebacate, acetyltetrabutyl citrate, triacetin, polyethylene glycol, castor oil, and other plasticizers well known in the art. The preferred plasticizer is dibutyl sebacate (DBS).

Several designs of drug containing patches for transdermal delivery are known in the art. One design suitable for hydrophilic drugs is the reservoir patch which is commonly composed of an impervious protective layer, a reservoir layer containing the drug composition, a drug-permeable membrane, an adhesive layer, a release strip and optionally a peelable disc. The reservoir layer is positioned between the impervious protective layer and one surface of the drug-permeable membrane. The whole surface or an edge portion of one side of adhesive layer is attached to the other surface of the drug-permeable membrane and optionally the central portion thereof is attached to the peelable disc. The other side of the adhesive layer is attached to the release strip. The peelable disc and the release strip are removed before use.

Another design suitable for a patch containing hydrophilic drugs is the drug-containing adhesive patch based on water soluble matrices in which the drug-containing layer is also containing adhesives as described hereinabove. In this type of patch, enhancing drug release is achieved by optimizing the proportion between the drug, polymer, cross linker, and plasticizer.

Unexpectedly, it is now disclosed that the system according to the present invention achieves delivery rates, in-vitro and in-vivo, that were not predicted according to the methods known in the art. Thus, when applying a granisetron-containing hydrogel patch, preferably within the size range of 3 to 9 $cm^2$ for a period of only 24 hours, the currently preferred system achieved clinically effective doses of anti-emetic medication that were sustained for more than 24 hours in human subjects. This turns out to be extremely beneficial for a patient especially when confronting clinical indications that necessitate prolonged anti-emetic medication as required for instance during a course of chemotherapy.

Advantageously, there was surprisingly low patient-to-patient variability in the blood levels of the anti-emetic drug when the drug was administered transdermally according to the present invention, as compared to oral and intravenous routes of administration. Thus, the present invention has overcome to a significant extent the inherent problem of patient variability.

Devices for Enhancing Transdermal Movement of a Hydrophilic Drug

The system of the present invention further contains an apparatus for enhancing transdermal movement of a substance. According to the principles of the invention the apparatus is used to generate a new skin environment through which a hydrophilic anti-emetic drug composition is delivered efficiently.

In a preferred embodiment of the present invention, the apparatus for enhancing transdermal movement of a substance using RF energy is as disclosed in U.S. Pat. No. 6,148,232 and continuations thereto, comprising: an electrode cartridge, optionally removable, comprising at least one electrode, and a main unit comprising a control unit. The main unit loaded with the electrode cartridge is also denoted herein ViaDerm.

The control unit is adapted to apply electrical energy to the electrode typically by generating current flow or one or more sparks when the electrode cartridge is in vicinity of the skin. The electrical energy in each electrode within the electrode array causes ablation of stratum corneum in an area beneath the electrode, thereby generating at least one micro-channel.

The control unit comprises circuitry which enables to control the magnitude, frequency, and/or duration of the electrical energy delivered to an electrode, in order to control current flow or spark generation, and consequently to control the dimensions and shape of the resulting micro-channel. Typically, the electrode cartridge is discarded after one use, and as such is designed for easy attachment to the main unit and subsequent detachment from the unit.

To minimize the chance of contamination of the cartridge and its associated electrodes, attachment and detachment of the cartridge is performed without the user physically touching the cartridge. Preferably, cartridges are sealed in a sterile cartridge holder, which is opened immediately prior to use, whereupon the main unit is brought in contact with a top surface of the cartridge, so as to engage a mechanism that locks the cartridge to the main unit. A simple means of unlocking and ejecting the cartridge, which does not require the user to touch the cartridge, is also provided.

Optionally the electrode cartridge may further comprise means to mark the region of the skin where micro-channels have been created, such that a medical patch can be precisely placed over the treated region of the skin. It is noted that micro-channel generation (when practiced in accordance with the techniques described in the above-cited U.S. patents or continuation patent applications to Avrahami et al., assigned to the assignee of the present patent application) does not generally leave any visible mark because even the large number of micro-channels typically generated are not associated with appreciable irritation to the new skin environment.

Methods for Using the System of the Invention

The current invention also provides a method of transdermal administration of anti-emetic drugs using the system of the invention. According to the invention, the method for forming new skin environment comprises a step of placing over the skin the apparatus of the invention for generating at least one micro-channel. Preferably, prior to generating the micro-channels, the treatment sites are swabbed with sterile alcohol pads. Preferably, the site is allowed to dry before treatment.

In preferred embodiments of the current invention, the type of apparatus used to generate micro-channels is disclosed in U.S. Pat. No. 6,148,232 and WO 02/092163. The apparatus, containing the electrode array, is placed over the site of treatment, the array is energized by RF energy, and treatment is initiated. In principle, the ablation and generation of micro-channels is completed within seconds. The apparatus is removed after micro-channels are generated at limited depth, preferably limited to the depth of the SC and the epidermis. A pharmaceutical composition, in the context of any patch known in the art that is suitable for usage in the system of the invention as described above, is attached to the new skin environment.

The present invention provides a method of transdermal administration of a hydrophilic anti-emetic agent from a pharmaceutical composition comprising generating at least one micro-channel in a region of the skin of a subject, affixing a patch to the region of skin in which the micro-channels are present, the patch comprises at least one hydrophilic layer comprising a therapeutically effective amount of a hydrophilic anti-emetic agent in a pharmaceutical composition.

The term "therapeutically effective amount" means the amount of active agent sufficient to produce the desired effect when applied topically over the duration of intended use. According to a preferred embodiment of the invention, transdermal administration of an anti-mimetic agent comprises attaining serum concentration of at least 1 ng/ml of the anti-mimetic agent. Preferably, the serum concentration of at least 1 ng/ml of the anti-emetic agents is maintained for at least 24 hrs. More preferably, the serum concentration of at least 1 ng/ml of the anti-emetic agent is maintained for at least 48 hrs.

According to preferred embodiments of the current invention, the micro-channels may be generated separately or simultaneously with the application of a medical patch. In some applications, the system may include a medical patch comprising an adhesive cut-out template which is placed on the skin, and through which the cartridge is placed to treat the region of skin exposed through the template. The anti-emetic medication, contained within a hydrophilic matrix, is attached to the template, which is to be placed over the treated region of skin. In these applications, after removing a protective backing, the template portion of the medical patch is placed on the skin and secured by the adhesive. An electrode cartridge is then affixed to the handle, the user holds the handle so as to place the cartridge against the region of skin inside the template, and the electrodes are energized to treat the skin. Subsequently, the cartridge is discarded. A protective covering is then removed from the medicated matrix by pulling on a tab projecting from the covering, so as to concurrently lift and place the medicated matrix over the treated region of skin. It is noted that the integration of the template and the patch into a single unit assists the user in accurately placing the medicated pad onto the treated area of skin. Utilizing the system of the invention in this manner becomes advantageous for disinfected applications.

For still other applications, an integrated electrode/medicated pad cartridge is used, to provide a practical apparatus as disclosed in International Patent Application No. WO 02/092163, which is assigned to the assignee of the present patent application and incorporated herein by reference, is also denoted MicroDerm. In these applications, the cartridge comprises an electrode array, a controlled unit and a medicated pad. Accordingly, no template is typically required. The user places the electrodes against the skin and this contact is sufficient to initiate current flow or spark formation within the electrode and the subsequent formation of micro-channels. An adhesive strip, coupled to the bottom of the medicated pad, comes in contact with and sticks to the skin when the electrodes are placed against the skin. A top cover on the medicated matrix is coupled to the electrode region of the cartridge, such that as the electrode region, fixed to the handle, is removed from the skin the top cover is pulled off the medicated pad and the pad is concurrently folded over the treated region of skin. This type of application eliminates the need for the user to touch any parts of the electrode cartridge or the medicated pad, thus substantially reducing or eliminating the likelihood of the user contaminating the apparatus.

In a preferred embodiment, current may be applied to the skin in order to ablate the stratum corneum. In one preferred embodiment, spark generation, cessation of spark generation, or a specific current level may be used as a form of feedback, which indicates that the desired depth has been reached and current application should be terminated. For these applications, the electrodes are preferably shaped and/or supported in a cartridge that is conducive to facilitating ablation of the stratum corneum and the epidermis to the desired depth, but not beyond that depth. Alternatively, the current may be configured so as to ablate the stratum corneum without the generation of sparks.

Generally preferred embodiments of the present invention typically incorporate methods and apparatus described in U.S. Pat. No. 6,611,706 entitled "Monopolar and bipolar current application for transdermal drug delivery and analyte extraction," which is assigned to the assignee of the present patent application and is incorporated by reference as if fully set forth herein. For example, this application describes maintaining the ablating electrodes either in contact with the skin, or up to a distance of about 500 microns therefrom. The application further describes spark-induced ablation of the stratum corneum by applying a field having a frequency between about 10 kHz and 4000 kHz, preferably between about 10 kHz and 500 kHz.

Alternatively or additionally, preferred embodiments of the present invention incorporate methods and apparatus described in International Patent Application WO 02/085451 entitled "Handheld apparatus and method for transdermal drug delivery and analyte extraction," which is incorporated by reference as if fully set forth herein.

Still further alternatively or additionally, preferred embodiments of the present invention incorporate methods and apparatus described in the above-cited U.S. Pat. No. 6,148,232 to Avrahami, which is assigned to the assignee of the present patent application and incorporated herein by reference.

In some preferred embodiments of the present invention, the cartridge supports an array of electrodes, preferably closely spaced electrodes, which act together to produce a high micro-channel density in an area of the skin under the cartridge. Typically, however, the overall area of micro-channels generated in the stratum corneum is small compared to the total area covered by the electrode array.

In further preferred embodiments of the present invention, a concentric electrode set is formed by employing the skin contact surface of the cartridge as a return path for the current passing from the electrode array to the skin. Preferably, the cartridge has a relatively large contact surface area with the skin, resulting in relatively low current densities in the skin near the cartridge, and thus no significant heating or substantial damage to the skin at the contact surface occurs.

In proximity to each electrode in the electrode array, by contrast, the high-energy applied field typically induces very rapid heating and ablation of the stratum corneum.

Having now generally described the invention, the same will be more readily understood through reference to the following examples, which are provided by way of illustration and are not intended to be limiting of the present invention.

EXAMPLES

Example 1

In Vitro Skin Permeation Study

Materials and Methods (i) Instruments and Materials

RF-micro-channels were generated at a density of 100 and 200 microelectrodes/cm² using ViaDerm.

Granisetron hydrochloride (Natco Pharma, Hyderabad, India) was freshly prepared in distilled water at concentrations of 1% to 5% w/v.

All solvents were HPLC grade (Merck, Germany).

(ii) Preparation of Granisetron Patches

A. Gel Based Patches

For application in the pre-clinical and clinical studies granisetron was incorporated into a cross-linked hydrogel sheet, commonly used as a wound dressing, of which composition is based on polyethylene oxide and water (VIGILON™, The Medical Supply Company Inc., NY, USA).

Hydrogel sheets of 1.4 cm² were incubated in a 5% w/v granisetron HCl solution for 2 hours, and immediately applied on the skin (held with a medical tape). The resulting granisetron concentration in the gel was 20±2 mg/patch, corresponding to a 2.5 fold increment of patches weight.

Gel based patches of granisetron were also formed based on polyvinylpyrrolidone (NUGEL™, Johnson & Johnson, USA) or based on hydroxy propyl methyl cellulose (HPMC). A representative formulation of granisetron embedded in HPMC hydrogel is shown in Table 1.

TABLE 1

Granisetron hydrogel matrix.

| Material | Function | Formulation (w/w %) |
|---|---|---|
| Granisetron HCl | Drug | 8.5% |
| Hydroxy propyl methyl cellulose (HPMC) | Polymer | 5.5% |
| Water | Solvent | 86% |

The preparation procedure was as follow: Granisetron HCl was dissolved in water using Heidolph RZR 2102 Control mixer at 400 rpm for 5 min. Hydroxy propyl methyl cellulose was added slowly until full dissolving of hydro gel in granisetron solution occurred. The mixture was left overnight to enable releasing of air bubbles.

For usage in the pharmacokinetics experiments (Example 2), the final concentration of granisetron was 5% (granisetron was soaked in a wound dressing hydrogel) whereas in the in vitro studies (Example 1), the concentration of granisetron was 1% w/v.

B. Drug-Containing Adhesive Patches

Granisetron was incorporated into a "drug-containing adhesive" patch by mixing the drug with acrylic based adhesive. The components of representative patches and the examples of formulations are given in Tables 2 and 3. The mixture is spread over a backing liner and dried (as known in the art of manufacturing of drug-containing adhesive patches). The formulations and preparation of drug-containing adhesive in combination with hydrogels is given in Table 3.

TABLE 2

Representative formulations for granisetron-containing adhesives

| Material | Function | Formulation (w/w %) | | |
|---|---|---|---|---|
| | | 173-4 | 179-1 | 179-3 |
| Succinic acid | Cross-linker | 1.03% | 0.85% | 1.1% |
| Granisetron HCl | Drug | 10% | 10% | 10% |
| *Eudragit ™ EPO | Adhesive | 15.5% | 16% | 16% |
| Dibutyl sebacate (DBS) | Plasticizer | 7% | 7.5% | 7.5% |
| Water | Solvent | 66.47% | 66.65% | 65.9% |

*Acrylic polymer on the basis of 2-dimethyl aminoethyl methacrylate, methyl methacrylate and n-butyl methacrylate.

The preparation procedure was as follow: Succinic acid was dissolved in water using Heidolph RZR 2102 Control mixer at 900 rpm (according to Manufacturer instructions) for 10 min. Granisetron HCl was added and mixed for 5 min.

EUDRAGIT™ EPO was then added gradually, within one hour. Dibutyl sebacate (DBS) was then added and stirring at 900 rpm was continued until a parameter depending on sample viscosity (defined by manufacturer as torque display) was equal to 5.3 N/cm. Release liner was coated with adhesive formulation using RK Coater set to 1000 µm and air-dried for 1 hour. Backing liner was then applied to coated liner.

TABLE 3

Representative formulations for hydrogel + granisetron adhesives

| Material | Formulation (w/w %) | |
|---|---|---|
| | 183/1 | 183/2 |
| Adhesive composition | | |
| Succinic acid | 0.76% | 0.77% |
| Granisetron HCl | 11.94% | 12.08% |
| *EUDRAGIT ™ EPO | 9.55% | 9.66% |
| DBS | 4.33% | 4.38% |
| Water | 70.74% | 71.6% |
| Hydro gel composition | | |
| Hydroxy propyl methyl cellulose | 0 | 1.51% |
| Polyvinylpyrrolidone | 2.69% | 0 |

The preparation procedure of the hydrogel granisetron-containing adhesives included the following steps:

Adhesive Formulation

Succinic acid was dissolved in water using Heidolph RZR 2102 Control mixer at 900 rpm for 10 min. Granisetron formulation was added and mixed for 5 min. EUDRAGIT™ EPO was added gradually within one hour. DBS was added and stirring at 900 rpm was continued until torque display was equal to 5.3 N/cm. Release liner was coated with the adhesive formulation using RK Coater set to 1000 µm and air-dried for 1 hour. Backing liner was applied to coated liner.

Granisetron Formulation 183/1

To 5 gram of dH₂O one gram of granisetron was added and then 0.45 gram of polyvinylpyrrolidone were added using magnetic stirrer. Then, 10 grams of the above adhesive were mixed.

Granisetron Formulation 183/2

To 5 gram of dH₂O one gram granisetron was added and then 0.45 gram of hydroxy prophyl methyl cellulose were added using magnetic stirrer. Then, 10 grams of the above adhesive were mixed. The mixture was left covered over night to allow air bubbles to be released.

(iii) Skin Permeation

The permeability of granisetron HCl through full thickness porcine ear skin was measured in vitro with a flow-through Franz diffusion cell system (Laboratory Glass Apparatus, Berkeley, Calif.). The diffusion area was 3.1 cm². Full-thickness porcine skin was excised from fresh ears of slaughtered white pigs (breeding of Landres and Large White, Kibbutz Lahav, Israel). Transepidermal water loss measurements (TEWL; DERMALAB® Cortex Technology, Hadsund, Denmark) were performed and only skin sections of TEWL levels less than 10 g/m² h were mounted in the diffusion cells. Sections were then placed on the receiver chambers with the stratum corneum facing upwards, and then the donor chambers were clamped in place. Skin micro-channeling, using ViaDerm, was performed in cells defined, prior to mounting, as the pretreatment group following the addition of drug solutions (0.5 ml of 1% granisetron HCl), using pipettes, into the donor chambers. Phosphate buffered saline (PBS, pH 7.4) or 10% EtOH in PBS was delivered through the receiver cells at a flow rate of 2 ml/hr. Samples from the receiver solutions were collected at predetermined time intervals for 24 hours and were kept at 4° C. until analyzed by HPLC.

Results

Figure 2:
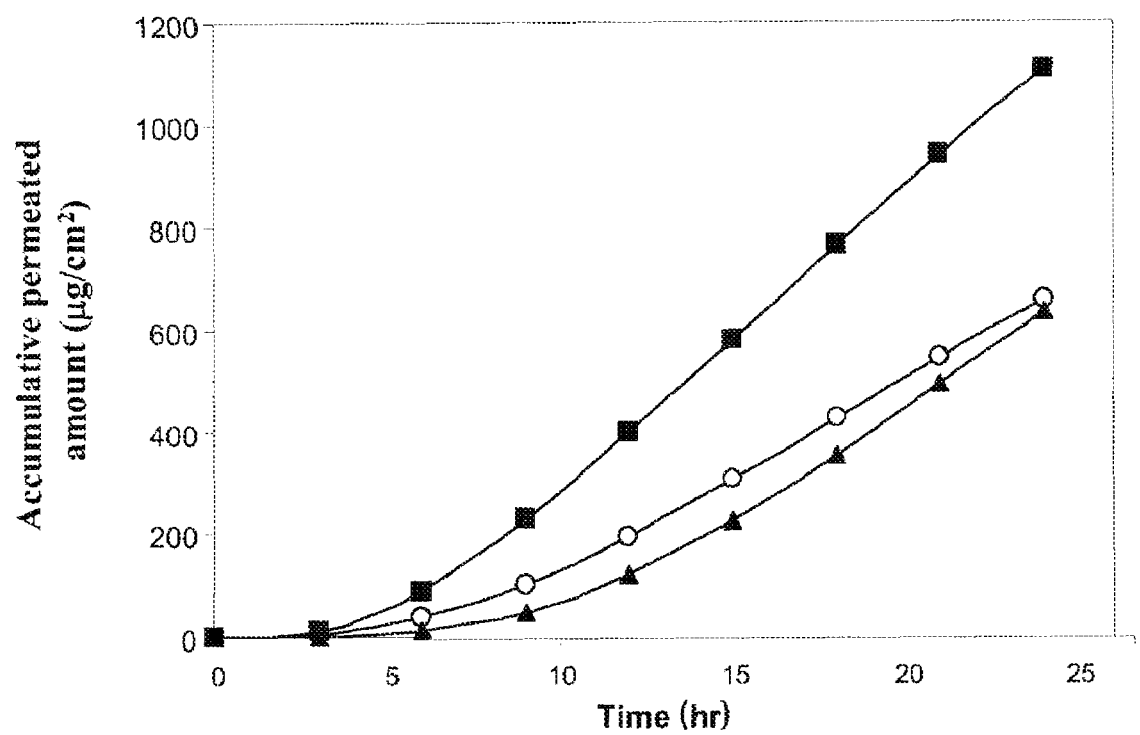
FIG. 2 presents permeation of granisetron, applied by means of a solution or hydroxypropyl methylcellulose (HPMC) based hydrogels through porcine ear skin after generation of micro-channels. Solution 10% (▲); HPMC gel 8.5% (○); HPMC gel 22 % (■).

Granisetron permeation through pig ear skin was tested using different hydrophilic gel patches: polyethylene oxide based patches (VIGILON™, The Medical Supply Company Inc., NY, USA), polyvinylpyrrolidone based patches (NU-GEL™, Johnson & Johnson, USA) and hydroxy propyl methyl cellulose (HPMC) based patches. Patches were placed over the skin for 24 hr. A gradual accumulation of permeated granisetron with time was observed in all types of patches. A comparison between the cross-linked hydrogels revealed that the delivery rate of granisetron achieved by using the commercial VIGILON™ patch is close to that of aqueous solutions of this drug (FIG. 1). The accumulative permeated amount of granisetron using HPMC gels with 8.5 w/w % granisetron (Table 1) was similar to that of granisetron solution (10% granisetron) and higher than that of the solution when granisetron concentration in the gel was 22 w/w % (FIG. 2). Similar results were achieved in a pre-clinical in vivo rat study.

Figure 3:
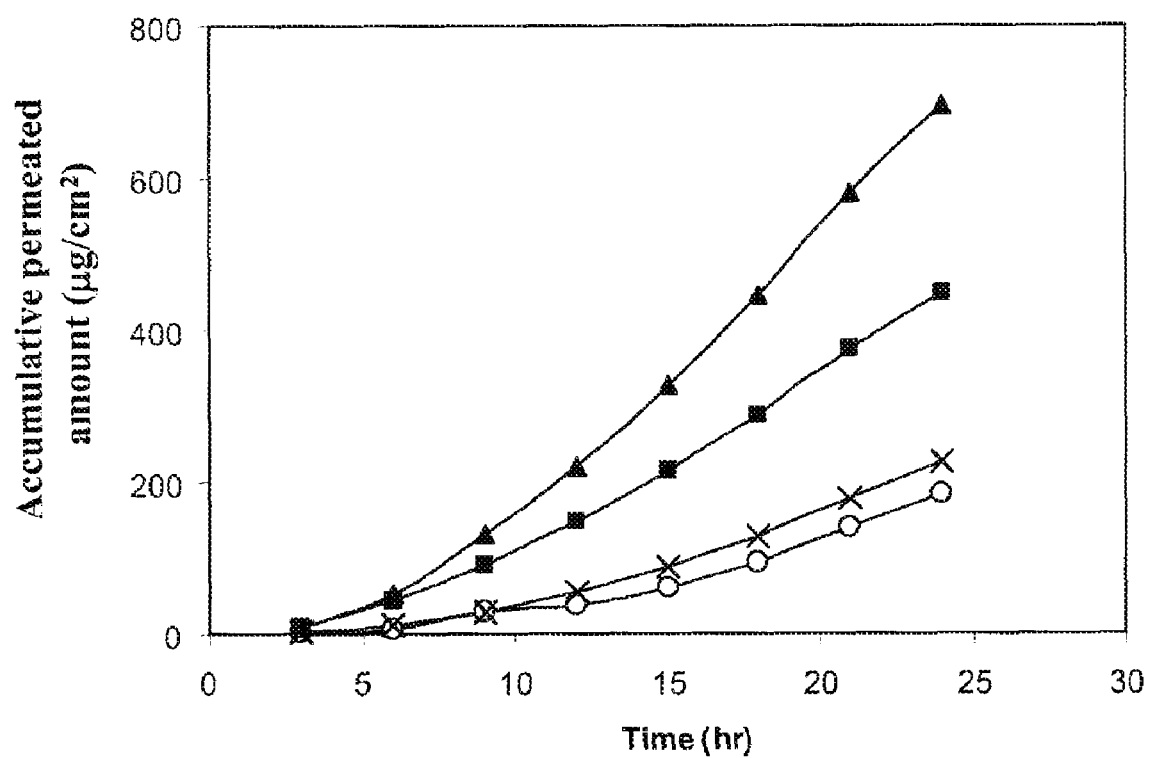
FIG. 3 exhibit the cumulative penetrating levels of granisetron, applied by means of granisetron-containing adhesive hydrogels and a commercially available hydrogel containing granisetron, through porcine ear skin after generation of micro-channels. 173-4 (○); 179-1 (■); 179-3 (x); VIGILON™ (▲).
Figure 4:
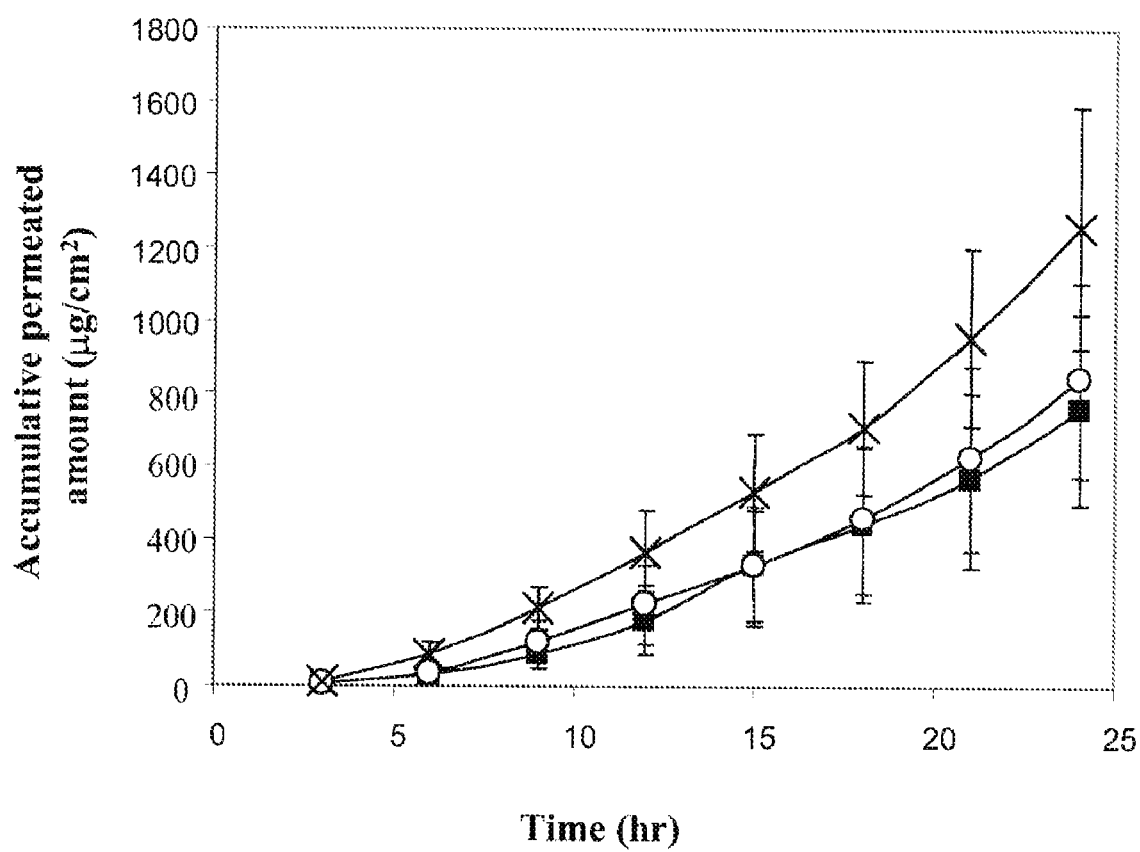
FIG. 4 exhibit the cumulative penetrating levels of granisetron, applied by means of granisetron-containing adhesive hydrogels and a commercially available hydrogel containing granisetron, through porcine ear skin after generation of micro-channels. 183/2 (■); 183/1 (○); VIGILON™ (x).

Granisetron permeation through the pig ear skin was tested using adhesive compositions of different formulations (see Tables 2 and 3 and FIGS. 3-4). A gradual accumulation of permeated granisetron with time was observed in all the adhesive formulations. The formulations in Table 2 contained higher concentrations of the adhesive substance EUDRAGIT™ EPO (15.5-16%; Rohm GmbH, Darmstadt, Germany) than the formulations in Table 3 (9.55-9.66%). The accumulative permeated amount of granisetron that was achieved using the formulations 173-4 and 179-3 were low with respect to the other formulations and to the commercial VIGILON™ hydrogel (FIGS. 3-4).

Example 2

Pre-Clinical Studies with Granisetron Patches and ViaDerm

Materials and Methods (i) Pharmacokinetic Studies of Transdermal Drug Delivery in Rats Male Sprague-Dawley rats (400-500 g, Harlan Laboratories Ltd., Jerusalem, Israel) were anesthetized (5 mg/kg ketamine i.p.) and were placed dorsally. Anesthesia was maintained until the end of the transdermal treatment and during blood sampling by injections of 0.1 ml ketamine and Xyalzine (60-80 mg/ml) every 30-40 min. The abdominal skin was shaved and cleaned with isopropyl alcohol. After 30 minutes, the transepidermal water loss was measured in order to verify skin integrity and RF-micro-channeling took place on the abdominal skin of a test group. Each experiment was accompanied by a control group of animals i.e. animals that did not experience the RF-micro-channeling procedure. A granisetron patch, made of a solution of 3% granisetron HCl soaked in a hydrogel sheet of 1.4 cm, was then attached to the skin surface for 24 hr in special containers glued to the skin by silicon medical glue. Blood samples were taken from the heart into heparinized tubes. After centrifugation, plasma samples were kept at −20° C. until analyzed for drug levels by HPLC.

(ii) HPLC Analysis of Samples from Receiver Solutions

Aliquots of 10 μl from each sample were injected into the HPLC system, equipped with the column as described below. Granisetron was detected at an excitation wavelength of 305 nm. HPLC procedure was conducted under the conditions of an isocratic mobile phase consisting of 40% acetonitrile and 60% sodium acetate at pH 4.2 and a flow rate of 0.75 ml/min. The cumulative drug permeation ($Q_t$) was calculated from the following equation:

$$Q_t = V_r C_t + \sum_{i=0-t} V_s C_i$$

where $C_t$ is the drug concentration of the receiver solution at each sampling time, $C_i$ is the drug concentration of the $i^{th}$ sample, and $V_r$ and $V_s$ are the volumes of the receiver solution and the sample, respectively. Data were expressed as the cumulative drug permeation per unit of skin surface area, $Q_t/S$ (for S=3.1 cm²).

(iii) HPLC Analysis of Plasma Extracts

The procedure was basically performed according to Kudoh et al, J. Chromatography 660(1994) p. 205. Phosphate buffer (500 μl, pH 7, 67 mM) was mixed with one ml plasma. Mixture was transferred on a 500 mg C-2 Bond Elute SPE cartridge (pre-washed consecutively with methanol, water and phosphate buffer, pH 7). The SPE cartridge was then washed with 2 ml of water and 2 ml of acetonitrile:water (40:60). The cartridge was dried under vacuum and granisetron was then eluted with 2 ml methanol followed by 2 ml methanol containing 1% trifluoroacetic acid. The combined eluate was dried at 40° C. under nitrogen and the residue was dissolved in 200 μl methanol:water (10:90). Aliquots (30 μl) from each sample were injected into the HPLC (1050 HP), equipped with a pre-packed $C_8$ column (BDS-Hypersil, UK; C-8 100×3.0 mm, 3 μm), an auto-sampler, and a fluorescence detector (Model 1046A). Granisetron was detected by excitation at 305 nm and emission at 365 nm. The samples were separated using an isocratic mobile phase consisting of 19% acetonitrile and 81% 0.1 M acetate buffer (pH 4.7) containing 10 mM hexanesulfonate and 0.23 g/l EDTA, at a flow rate of 0.3 ml/min. Calibration curves (peak area versus drug concentration) were linear over the range 2-100 ng/ml.

Results

Figure 5:
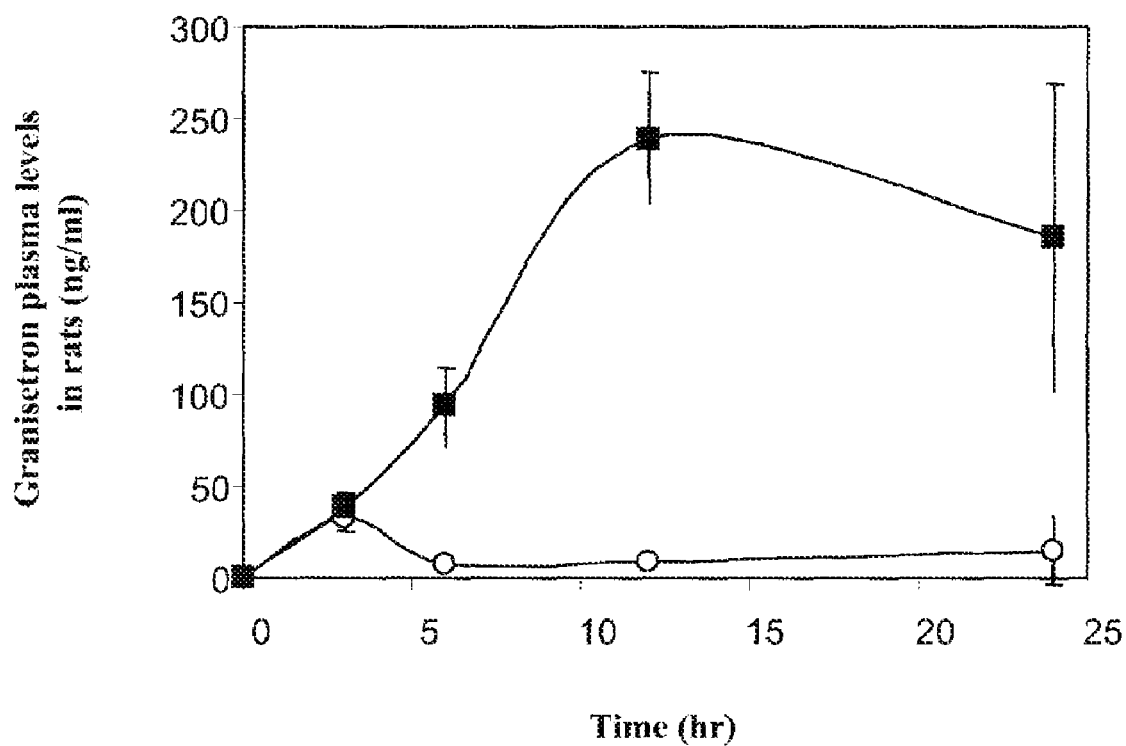
FIG. 5 shows plasma levels of granisetron, in rats treated by hydrogel patches, in the presence (■) or absence (control) (○) of pre-generated micro-channels.

Anesthetized rats were either not-treated or treated with ViaDerm, and thereafter a 3% granisetron HCl hydrogel was applied on the test skin areas. Drug levels were determined in blood samples withdrawn over a period of 24 h. Granisetron was accumulated in the plasma of rats that were pretreated with ViaDerm. The high level of this drug (above 200 ng/ml), which was gradually achieved during the first 12 hours after application of the granisetron+hydrogel patch, was maintained for additional 12 hours. In contrast, in rats that were not treated with ViaDerm, only a very small peak (lower than 50 ng/ml) was detected at 2.5 hours after application of the granisetron+hydrogel patch (FIG. 5).

Example 3

Clinical Studies with Granisetron Patches and ViaDerm

Usage of granisetron hydrophilic patches with ViaDerm was tested in several studies. The purpose of the first phase study was to determine patch size per drug dose. The target population for the study was healthy male and female volunteers who signed informed consent and fulfilled the following inclusion criteria:
1. Are capable of understanding and signing an informed consent
2. Are between the ages of 18 and 60 years
3. Are medically stable
4. Have fair skin color that enable to observe erythema and/or edema.
5. Have two hands with no obvious marks, bruises, cuts, and abrasions on the back of the hand.
6. Hemoglobin more than 12 gm % in females and more than 14 gm % in males.

Granisetron HCl patches were applied on the skin of the upper arm and fore arm of healthy adult volunteers. Patches were composed of a cross-linked hydrogel sheet containing 3% active drug. Irritation was examined by monitoring edema and erythema as described in Example 6.

The purpose of this experiment was to determine the patch size per drug dose, which is required to reach a mean $C_{max}$ of at least 4 ng/ml, in three volunteers. Three types of patches were tested: 2.8 cm$^2$, 5.6 cm$^2$ and 8.4 cm$^2$. TEWL measurements were conducted at the treatment site before and immediately after the ViaDerm treatment. The treatment sites where then covered with the granisetron patches for 24 hours. TEWL measurements were also conducted 25 hours and 72-96 hours after the ViaDerm treatment in order to monitor erythema and edema. Blood samples were collected at the following times periods: 0, 1, 2, 3, 4, 6, 9, 12, 16, and 24 hr post ViaDerm+patch application.

Figure 6:
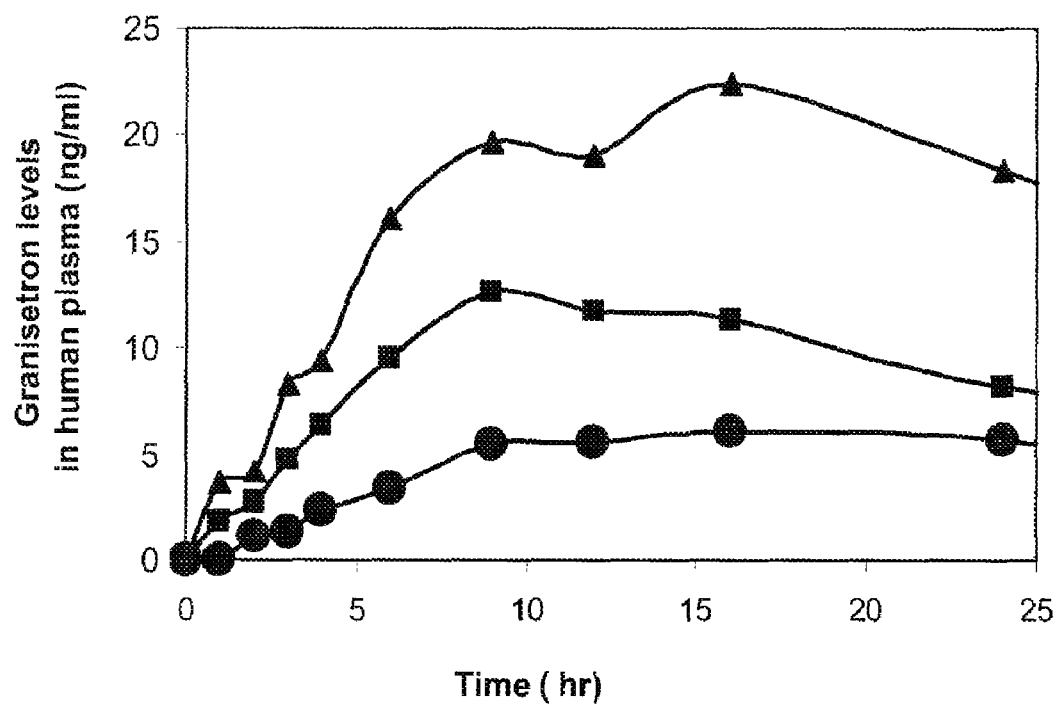
FIG. 6 presents clinical results of granisetron plasma levels upon treatment with granisetron-containing hydrogel patches of different sizes. The patches: 2.8 cm$^2$ (●); 5.6 cm$^2$ (■); 8.4 cm$^2$ (▲).
Figure 7:
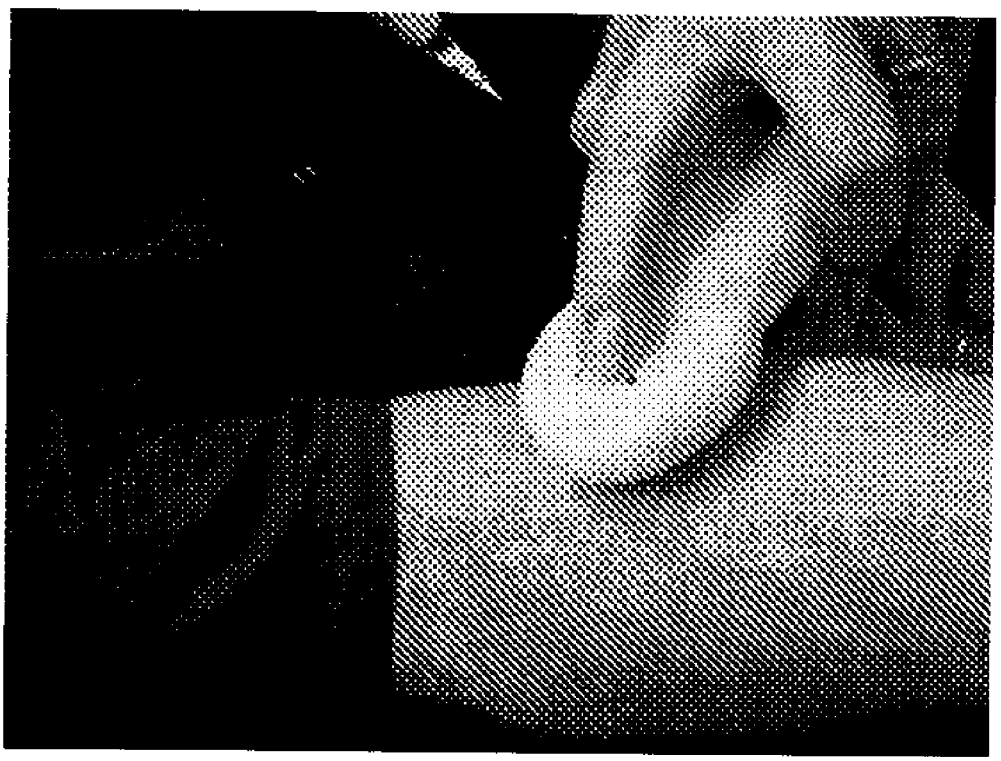
FIG. 7 is a photograph demonstrating an application of ViaDerm.

The results displayed a clear dose dependent increase during the first 9 hr after application of the granisetron patches (FIG. 6). The maximal concentration of granisetron in human plasma linearly correlated with the size of patch and consequently of skin area covered with the patch. These maximal granisetron levels, for each patch size, maintained constant to a certain extent until 24 hr after application of the granisetron patches. The maximal response to erythema and to edema was below 1, accounting for a negligible response, similarly to the results obtained for ViaDerm alone (refer to Example 6). Application of a granisetron patch covering a skin area of 5.6 cm$^2$ resulted in a high maximal plasma concentration (above 4 ng/ml), which remained high for at least 24 hr. Application of the ViaDerm apparatus on the forearm of a volunteer, for the generation of micro-channels, is illustrated in FIG. 7.

Example 4

Clinical Bioavailability Studies with Granisetron Patches and ViaDerm

The bioavailability of granisetron patches and ViaDerm treatment was tested in a population of healthy male and female volunteers who signed informed consent and fulfilled the inclusion criteria (see Example 3). Granisetron HCl patches were applied on the skin of the upper arm and fore arm of healthy adult volunteers. Patches were composed of a cross-linked hydrogel sheet containing 3% active drug. Irritation was examined by monitoring edema and erythema as described in Example 6.

The bioavailability of granisetron patches was compared to an oral delivery (1 tablet of 1 mg granisetron, twice daily). The control group did not receive a ViaDerm treatment prior to application of granisetron patches. The size of granisetron patch chosen for this study was 5.6 cm$^2$ (as described in Example 3 hereinabove). The experiment was conducted with six subjects, in a crossover manner. Each subject received four different treatments, i.e. various administration methods at various sites of patch application, with at least six days washout period between treatments.

Figure 8:
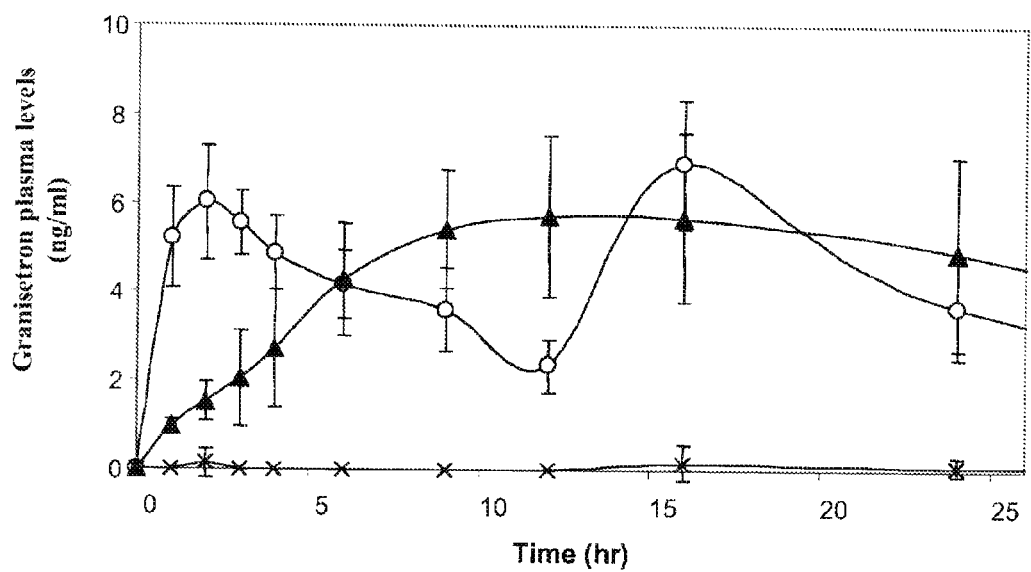
FIG. 8 exhibits clinical results of granisetron plasma levels, following different methods of administration. Oral administration (○); ViaDerm treatment (▲); No ViaDerm (x).

The ViaDerm enhancement of transdermal delivery of granisetron was clearly demonstrated in the comparison between plasma levels of the study group that was treated with ViaDerm to the control group without ViaDerm pretreatment (FIG. 8). Plasma levels of granisetron remained high (above 4 ng/ml) for over 24 hours in subjects treated with ViaDerm+granisetron-patch. The oral-treatment group demonstrated high levels of granisetron in the plasma (above 4 ng/ml) only for short time periods and the overall profile of granisetron in the plasma of this group was unsteady. These results clearly exhibited the sustained release effect achieved by the system of the present invention. Using ViaDerm and granisetron patches produced a minor irritation, similar to that obtained using the ViaDerm alone (see Example 6).

Example 5

ViaDerm Apparatus: Specifications and Performance in vivo

Figure 9:
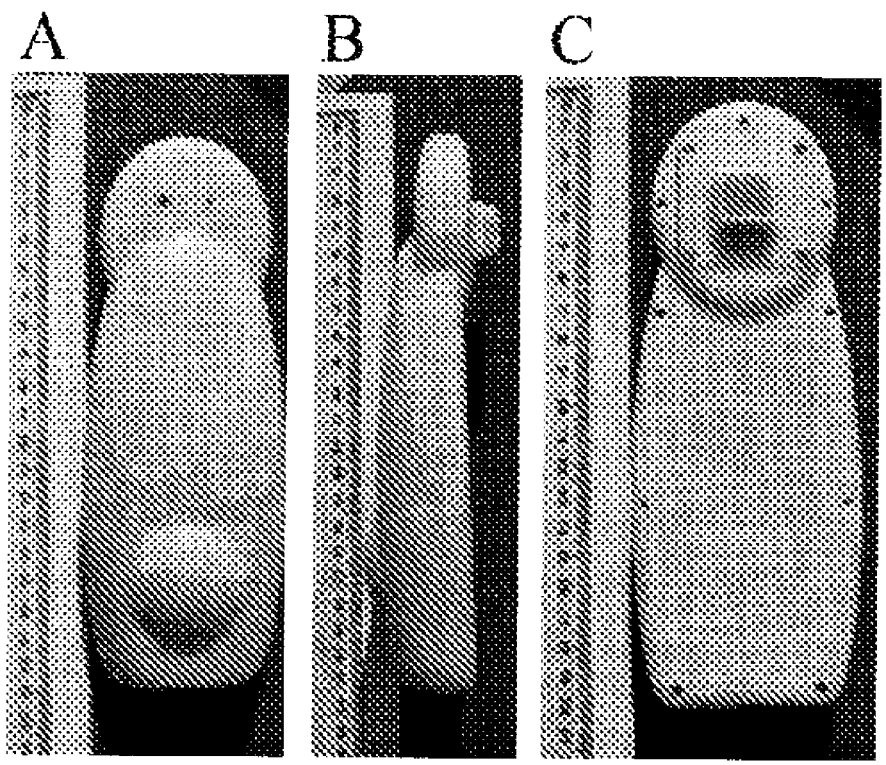
FIG. 9 exhibits top (a), side (b) and bottom (c) views of a ViaDerm apparatus.
Figure 10:
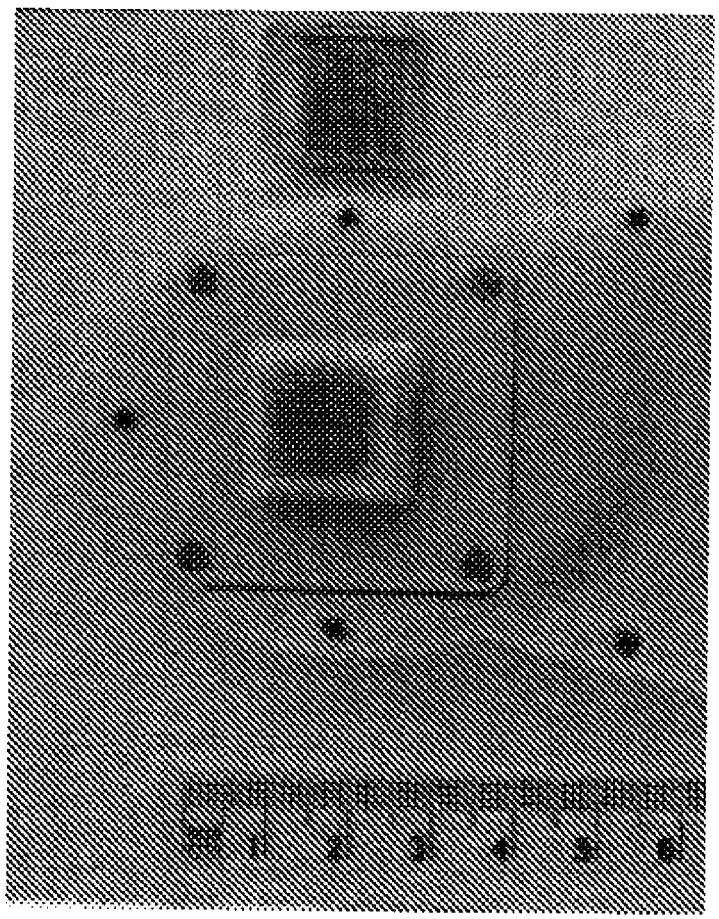
FIG. 10 is a photograph of the electrode cartridge containing an array of microelectrodes and attached to the top part of the main unit of a ViaDerm apparatus.

The ViaDerm apparatus that was used to generate microchannels in the pre-clinical and clinical studies described in the above examples is disclosed in U.S. Pat. No. 6,148,232; WO 02/085451 and in WO 02/092163. In brief, ViaDerm is comprised of the following:
1. A reusable main unit comprising a control unit, which generates an RF electrical current (FIG. 9).
2. A disposable electrode cartridge (FIG. 10) comprising an array of microelectrodes attached onto the end of the main unit.

Figure 11:
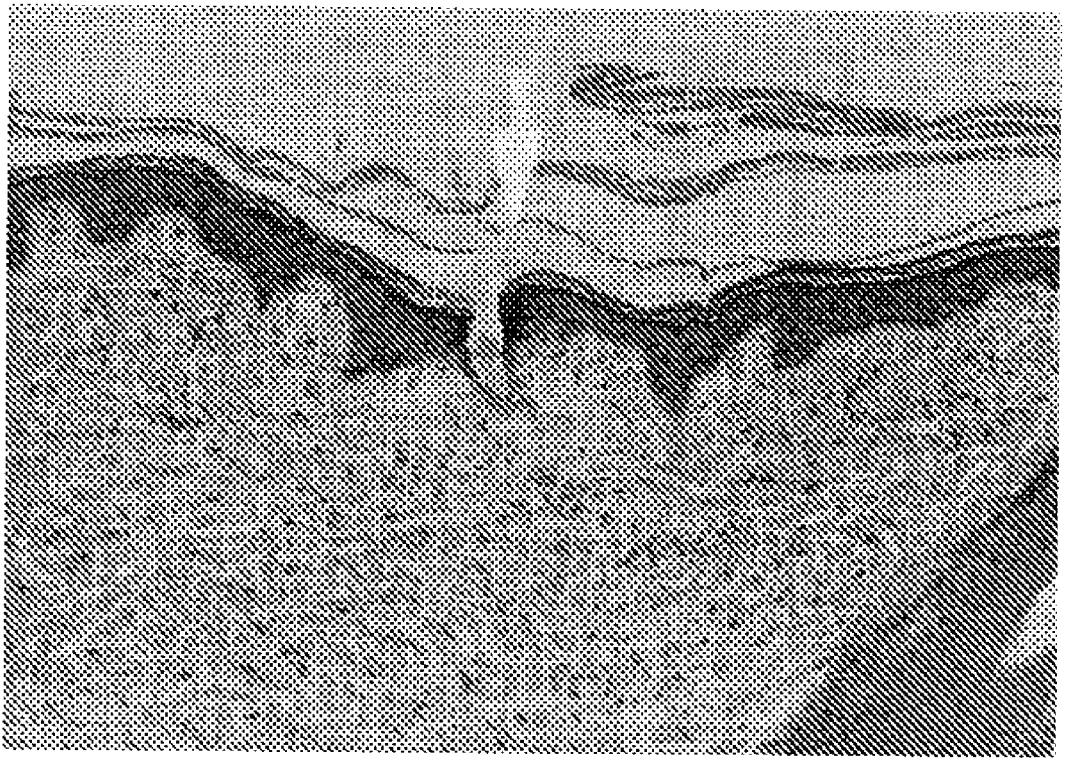
FIG. 11 is a hematoxylin and eosin stained histological section of porcine ear skin treated by ViaDerm.

Histological studies of micro-channels formed by ViaDerm within a porcine skin showed that the dimensions of the micro-channels are controllable and precise: each microchannel was 30 μm in width and 50-100 μm in depth. In the porcine skin, wherein the epidermis depth is about 40 μm, these micro-channels penetrated into the dermis. However in humans, in whom epidermis depth is about 100 μm, such micro-channels reside within the limits of the epidermis. In addition, it should be noted that the micro-channels were very localized, and the skin surrounding the micro-channels maintained its normal structure (FIG. 11).

Figure 12:
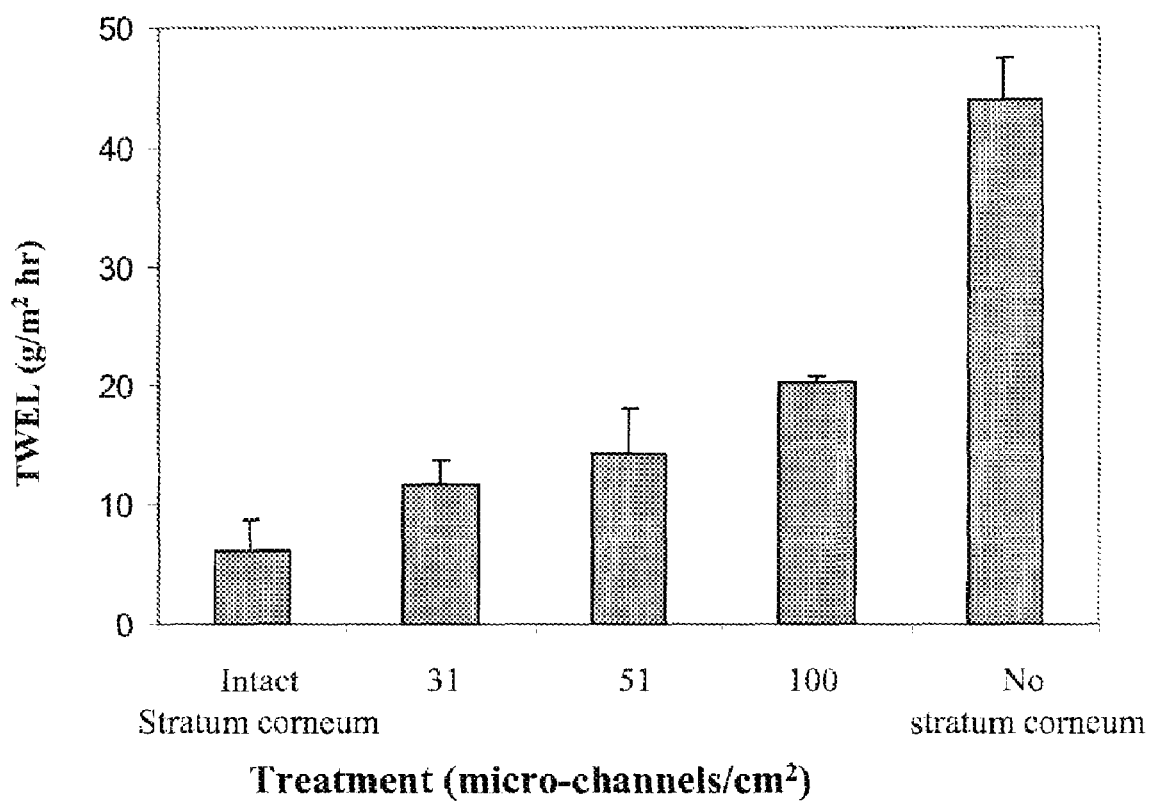
FIG. 12 presents the transepidermal water loss (TEWL) from porcine ear skin, after generation of micro-channels or after removal of the stratum corneum.
Figure 13A:
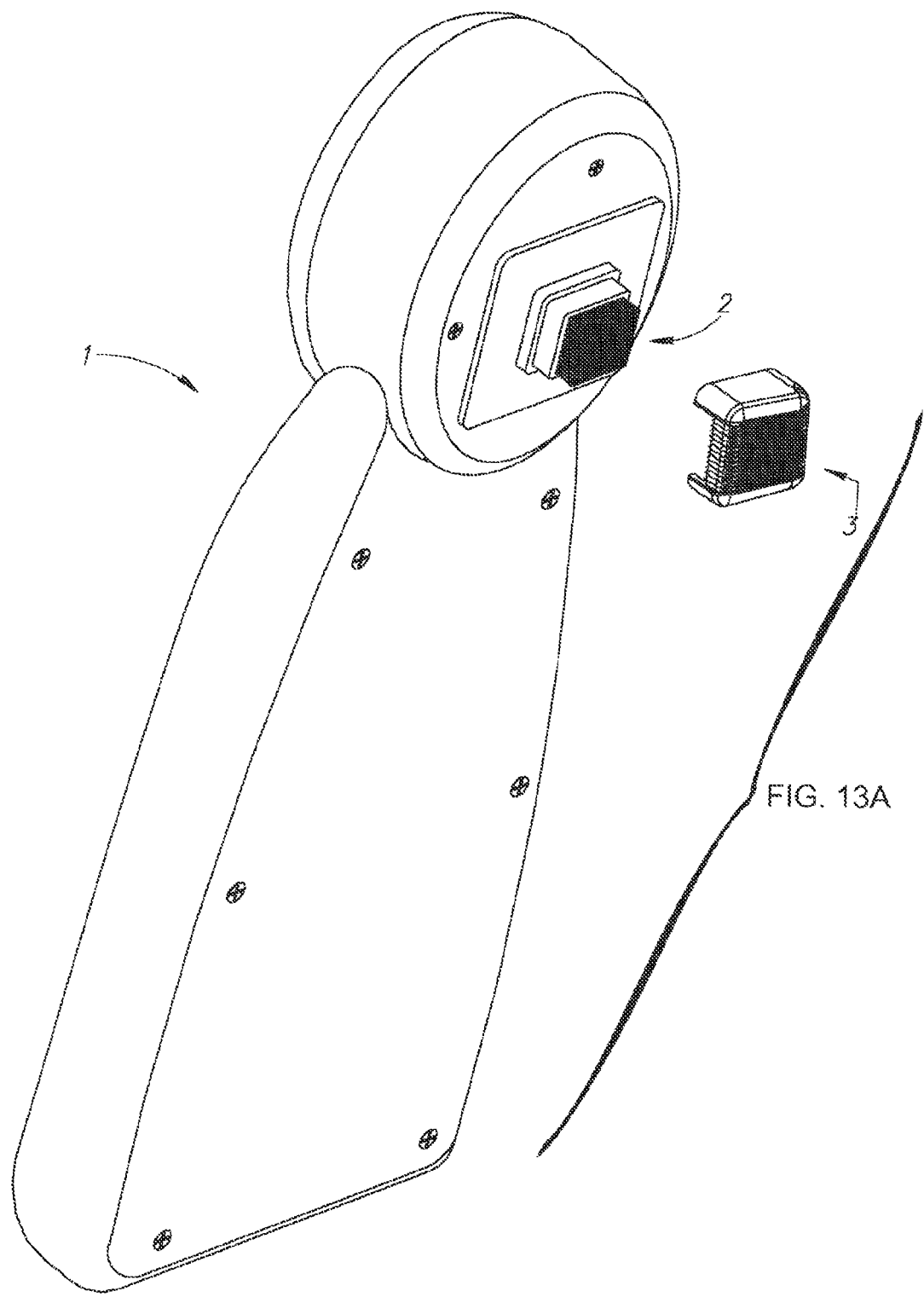
FIGS. 13A and B show the main unit (1) containing electrical contacts (2) through which the electrical energy from the main unit is transferred to the electrode cartridge (3) (A) and an enlarged view of a region of the electrode cartridge (3) which shows the electrodes (4) (B).
Figure 13B:
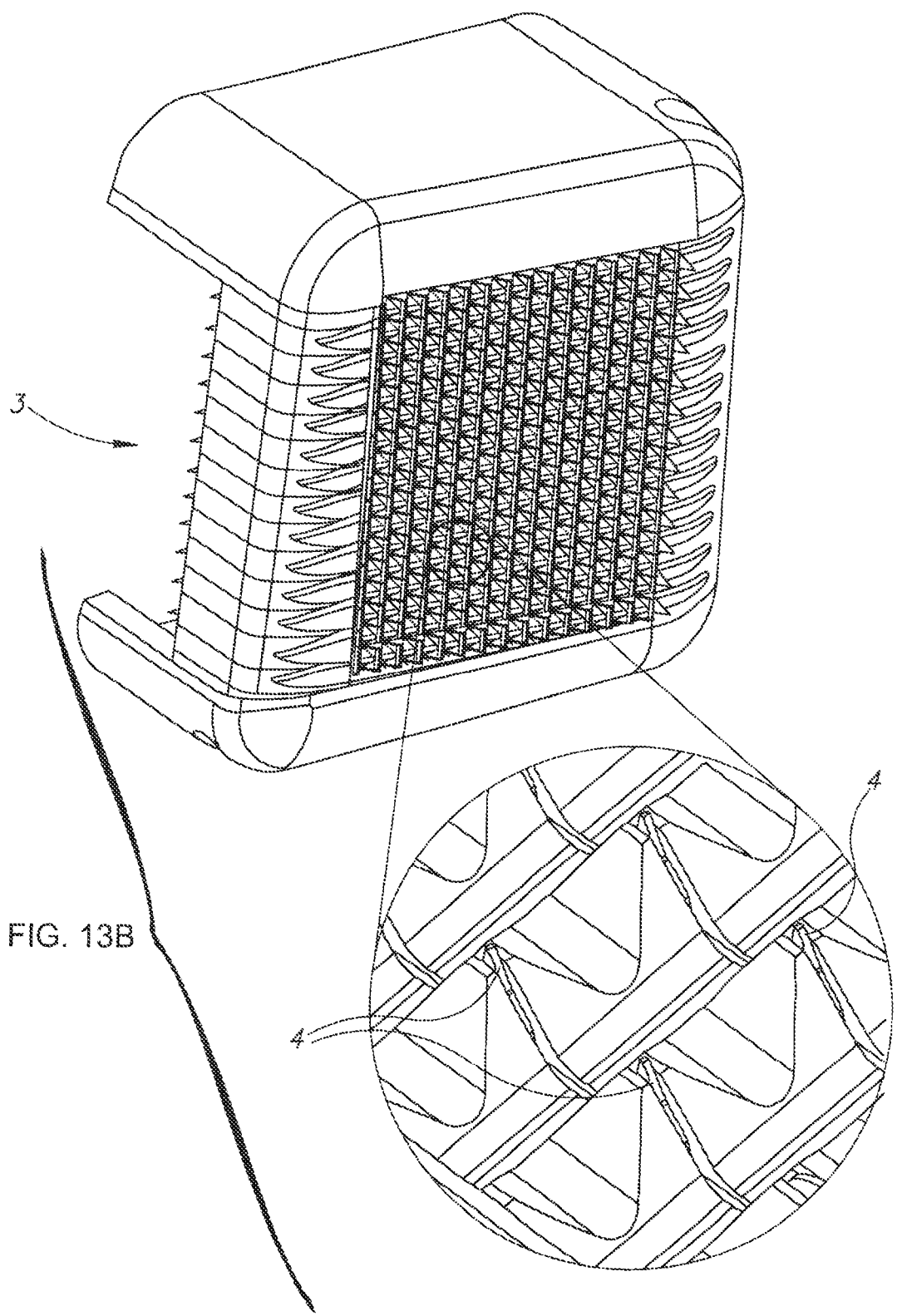

TEWL was measured in skin sections of porcine ear after generating different quantities of micro-channels (FIG. 12). TEWL linearly increased with increasing the number of micro-channels.

Example 6

Clinical Studies of ViaDerm Performance

Materials and Methods

Study subjects. ViaDerm performance was assessed by a study conducted with twenty healthy, adult volunteers, 10 males and 10 females. The study was conducted at ClinRx a Clinical research organization under Good Laboratory Practice (GLP) standards. Each subject received 10 treatments, in a randomized manner such that a given treatment was applied to different subjects and/or in each subject at different sites.

Treatment protocol. The treatment sites were the inner arm and hand. Each treatment included the following steps: preparing the skin (cleaning); measuring TEWL ($T_{0-}$) at a treatment site and an adjacent site; placing ViaDerm upon the treatment site and activating the electrodes with controlled RF electrical energy; measuring TEWL immediately at the treatment site and the adjacent site; Scoring for erythema, edema and tolerability ($T_{0+}$), at the treatment site; covering the treatment site with a sterile hydrogel (VIGILON™, The Medical Supply Company Inc., NY, USA) patch; Removing the patch at T=24 hr; measuring TEWL at the treatment site and the adjacent site; Scoring for erythema and edema at the treatment site at T=25 hr and 48 hr.

ViaDerm performance. Measuring Transdermal Water Loss (TEWL) at a skin site treated with ViaDerm in comparison to an adjacent untreated skin assessed formation of micro-channels. Safety of ViaDerm was evaluated by measuring irritation (erythema and edema) at the treatment site using a scale of zero to eight in accordance with Draize irritation index (Table 4). The response to irritation induced by ViaDerm was assessed by a Cumulative Irritation Index (Table 5). Skin tolerability was studied by measuring pain on a 100 mm Visual Analog Scale (VAS) following ViaDerm treatment.

Results a. Safety Evaluation.

Erythema was observed at sites treated with ViaDerm and covered with a patch for 24 hr. This erythema disappeared 24 hr after removal of the patch. Erythema was not observed in non-treated adjacent sites. The maximal mean value of erythema was 0.81 accounting for a very slight erythema according to Table 5. The different application sites exhibited similar irritation scores.

Edema was observed at sites treated with ViaDerm and covered with a patch for 24 hr. This edema disappeared 24 hr after removal of the patch. Edema was not observed in non-treated adjacent sites. The maximal mean value of edema was 0.25 accounting for negligible edema according to Table 4. The different application sites exhibited similar irritation scores.

The maximal mean combined irritation index (erythema and edema) was 0.75 for the ViaDerm treatment sites when occluded and 0.5 for the adjacent non-occluded sites accounting for a minor response (Table 5).

TABLE 4

Draize irritation index.

| | Grade |
|---|---|
| Erythema and Eschar Formation | |
| No erythema | 0 |
| Very slight erythema (barely perceptible) | 1 |
| Well defined erythema | 2 |
| Moderate to severe erythema | 3 |
| Severe erythema (beet redness) to eschar formation preventing grading of erythema | 4 |
| Edema formation | |
| No edema | 0 |
| Very slight edema (barely perceptible) | 1 |
| Slight edema (edges of area well defined by definite raising) | 2 |
| Moderate edema (raised approximately 1 mm) | 3 |
| Severe edema (raised more than 1 mm and extending beyond area of exposure) | 4 |
| Total possible score for irritation | 8 |

TABLE 5

Cumulative Irritation Index.

| Response category | Mean Score |
|---|---|
| Negligible | 0 to 0.4 |
| Slight | 0.5 to 1.9 |
| Moderate | 2.0 to 4.9 |
| Severe | 5.0 to 8.0 | b. Tolerability Evaluation

Pain scores were in the range of 0-50 mm. The pain score per subject was an average from 10 ViaDerm applications. The average values (per site of treatment) ranged from 2.1 mm to 7.02 mm. Those values are considered negligible.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention. Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

What is claimed is:

1. A system for transdermal delivery of a hydrophilic anti-emetic agent from a pharmaceutical composition comprising:
   an apparatus for facilitating transdermal delivery of a hydrophilic anti-emetic agent through skin of a subject, said apparatus comprises:
   (a) an electrode cartridge comprising at least one electrode; and
   (b) a main unit comprising a control unit which is adapted to apply electrical energy to the electrode when the electrode is in vicinity of the skin, enabling ablation of stratum corneum in an area beneath the electrode, thereby generating at least one micro-channel in an area on the skin of the subject;
   and a separate patch that does not receive electrical energy from the apparatus, the patch is adapted to be applied to the area on the skin after the at least one microchannel is generated, said patch comprising at least one hydrophilic layer comprising a hydrophilic polymer and a therapeutically effective amount of the hydrophilic anti-emetic agent in a pharmaceutical composition, devoid of permeation enhancers.

2. The system according to claim 1, wherein the patch further comprises at least one layer selected from a backing layer, an adhesive, and a release liner.

3. The system according to claim 1, wherein the hydrophilic polymer is selected from the group consisting of cellulose, hydroxy cellulose, carboxymethyl cellulose, hydroxyethyl cellulose, hydroxypropyl cellulose, hydroxypropylmethyl cellulose, polysaccharides, chitin, chitosan, diacylated chitin, gum acacia, agarose, carrageenan, gelatin, gum tragacanth, alginate, karaya gum, veegum, pectin, hyaluronic acid, pluronic acid, maltodextrin, polyvinylpyrrolidone, polyglycolic acid, polyoxyethylene, polyoxypropylene, colloidal silicon dioxide, polyvinyl alcohol, polyacrylamide, polyacrylic acid, polyacrylates, methacrylate polymers, and fumed silica.

4. The system according to claim 1, wherein the electrode cartridge is removable.

5. The system according to claim 1, wherein the electrode cartridge comprises a plurality of electrodes capable of generating a plurality of micro-channels of uniform shape and dimensions.

6. The system according to claim 1, wherein the electrical energy is of radio frequency.

7. The system according to claim 1, wherein the anti-emetic agent is selected from the group consisting of dopamine antagonists, acetylcholine receptor antagonists, 5-hydroxytryptamine receptor antagonists, and pharmaceutically acceptable salts, and hydrates thereof.

8. The system according to claim 7, wherein the 5-hydroxytryptamine receptor antagonist is selected from the group consisting of hydrophilic derivatives of granisetron, ondansetron, lerisetron, dolasetron, tropisetron, itasetron, and ramosetron.

9. The system according to claim 8, wherein the 5-hydroxytryptamine receptor antagonist is granisetron hydrochloride.

10. The system according to claim 1, wherein the pharmaceutical composition further comprises at least one component selected from the group consisting of a plasticizer, a cross-linker, a buffering agent, a stabilizer, and an anti-oxidant.

11. A method for transdermal administration of a hydrophilic anti-emetic agent comprising: generating at least one micro-channel in an area of skin of a subject; and affixing a patch to the area of skin where the at least one micro-channel is present, the patch comprises at least one hydrophilic layer comprising a hydrophilic polymer and a therapeutically effective amount of a hydrophilic anti-emetic agent in a pharmaceutical composition, devoid of permeation enhancers.

12. The method according to claim 11, wherein generating the at least one micro-channel is performed by an apparatus comprising:
   an electrode cartridge comprising at least one electrode; and
   a main unit comprising a control unit which is adapted to apply electrical energy to the electrode when the electrode is in vicinity of the skin, enabling ablation of stratum corneum in an area beneath the electrode, thereby generating at least one micro-channel.

13. The method according to claim 12, wherein the electrode cartridge is removable.

14. The method according to claim 12, wherein the electrode cartridge comprises a plurality of electrodes capable of generating a plurality of micro-channels of uniform shape and dimensions.

15. The method according to claim 12, wherein the electrical energy is of radio frequency.

16. The method according to claim 11, wherein the anti-emetic agent is selected from the group consisting of dopamine antagonists, acetylcholine receptor antagonists, 5-hydroxytryptamine receptor antagonists, and pharmaceutically acceptable salts, and hydrates thereof.

17. The method according to claim 16, wherein the 5-hydroxytryptamine receptor antagonist is selected from the group consisting of hydrophilic derivatives of granisetron, ondansetron, lerisetron, dolasetron, tropisetron, itasetron, and ramosetron.

18. The method according to claim 17, wherein the 5-hydroxytryptamine receptor antagonist is granisetron hydrochloride.

19. The method according to claim 11, wherein the pharmaceutical composition further comprises at least one component selected from the group consisting of a plasticizer, a cross-linker, a buffering agent, a stabilizer, and an anti-oxidant.

20. The method according to claim 11, wherein the patch further comprises at least one layer selected from the group consisting of a backing layer, an adhesive, and a release liner.

21. The method according to claim 11, wherein the hydrophilic polymer is selected from the group consisting of cellulose, hydroxy cellulose, carboxymethyl cellulose, hydroxyethyl cellulose, hydroxypropyl cellulose, hydroxypropylmethyl cellulose, polysaccharides, chitin, chitosan, diacylated chitin, gum acacia, agarose, carrageenan, gelatin, gum tragacanth, alginate, karaya gum, veegum, pectin, hyaluronic acid, pluronic acid, maltodextrin, polyvinylpyrrolidone, polyglycolic acid, polyoxyethylene, polyoxypropylene, colloidal silicon dioxide, polyvinyl alcohol, polyacrylamide, polyacrylic acid, polyacrylates, methacrylate polymers, and fumed silica.

22. A method of transdermal administration of a hydrophilic anti-emetic agent comprising: generating at least one micro-channel in an area of the skin of a subject; and thereafter affixing a patch to the area of skin of the subject where the at least one micro-channel is present, wherein the patch comprises at least one hydrophilic layer comprising a hydrophilic polymer and a therapeutically effective amount of a hydrophilic anti-emetic agent in a pharmaceutical composition, devoid of permeation enhancers, the hydrophilic anti-emetic agent capable of diffusing through the at least one micro-channel to achieve a therapeutically effective serum concentration of at least 1 ng/ml in the subject.

23. The method according to claim 22 wherein the therapeutically effective serum concentration of the anti-emetic agent of at least 1 ng/ml is maintained for at least 24 to 48 hours.

24. The method according to claim 22, wherein generating the at least one micro-channel is performed by an apparatus comprising:
   an electrode cartridge comprising at least one electrode; and
   a main unit comprising a control unit which is adapted to apply electrical energy to the electrode when the electrode is in vicinity of the skin, enabling ablation of stratum corneum in an area beneath the electrode, thereby generating at least one micro-channel.

25. The method according to claim 24, wherein the electrode cartridge is removable.

26. The method according to claim 24, wherein the electrode cartridge comprises a plurality of electrodes capable of generating a plurality of micro-channels of uniform shape and dimensions.

27. The method according to claim 24, wherein the electrical energy is of radio frequency.

28. The method according to claim 22, wherein the anti-emetic agent is selected from the group consisting of dopamine antagonists, acetylcholine receptor antagonists, 5-hydroxytryptamine receptor antagonists, and pharmaceutically acceptable salts, and hydrates thereof.

29. The method according to claim 28, wherein the 5-hydroxytryptamine receptor antagonist is selected from the group consisting of hydrophilic derivatives of granisetron, ondansetron, lerisetron, dolasetron, tropisetron, itasetron, and ramosetron.

30. The method according to claim 29, wherein the 5-hydroxytryptamine receptor antagonist is granisetron hydrochloride.

31. The method according to claim 22, wherein the pharmaceutical composition further comprises at least one component selected from the group consisting of a plasticizer, a cross-linker, a buffering agent, a stabilizer, and an anti-oxidant.

32. The method according to claim 22, wherein the patch further comprises at least one layer selected from the group consisting of a backing layer, an adhesive, and a release liner.

33. The method according to claim 22, wherein the hydrophilic polymer is selected from the group consisting of cellulose, hydroxy cellulose, carboxymethyl cellulose, hydroxyethyl cellulose, hydroxypropyl cellulose, hydroxypropylmethyl cellulose, polysaccharides, chitin, chitosan, diacylated chitin, gum acacia, agarose, carrageenan, gelatin, gum tragacanth, alginate, karaya gum, veegum, pectin, hyaluronic acid, pluronic acid, maltodextrin, polyvinylpyrrolidone, polyglycolic acid, polyoxyethylene, polyoxypropylene, colloidal silicon dioxide, polyvinyl alcohol, polyacrylamide, polyacrylic acid, polyacrylates, methacrylate polymers, and fumed silica.

* * * * *